(12) United States Patent
Serrero

(10) Patent No.: US 7,815,906 B2
(45) Date of Patent: *Oct. 19, 2010

(54) COMPOSITIONS AND METHODS FOR RESTORING SENSITIVITY TO TREATMENT WITH HER2 ANTAGONISTS

(75) Inventor: Ginette Serrero, Ellicott City, MD (US)

(73) Assignee: A & G Pharmaceutical, Inc., Columbia, MD (US)

(*) Notice: Subject to any disclaimer, the term of this patent is extended or adjusted under 35 U.S.C. 154(b) by 88 days.

This patent is subject to a terminal disclaimer.

(21) Appl. No.: 12/141,749

(22) Filed: Jun. 18, 2008

(65) Prior Publication Data

US 2009/0010931 A1 Jan. 8, 2009

Related U.S. Application Data

(63) Continuation of application No. 10/902,374, filed on Jul. 30, 2004, now Pat. No. 7,674,460.

(60) Provisional application No. 60/491,536, filed on Aug. 1, 2003, provisional application No. 60/547,791, filed on Feb. 27, 2004.

(51) Int. Cl.
A61K 39/395 (2006.01)
A61K 39/00 (2006.01)

(52) U.S. Cl. .............. 424/138.1; 424/141.1; 424/155.1

(58) Field of Classification Search .............. None
See application file for complete search history.

(56) References Cited

U.S. PATENT DOCUMENTS

| | | | |
|---|---|---|---|
| 5,416,192 A | 5/1995 | Shoyab et al. | |
| 5,709,858 A | 1/1998 | Godowski et al. | |
| 5,725,856 A | 3/1998 | Hudziak et al. | |
| 6,511,986 B2 | 1/2003 | Zhang et al. | |
| 6,558,668 B2 | 5/2003 | Liau | |
| 6,570,002 B1 | 5/2003 | Hardwick et al. | |
| 6,586,395 B1 | 7/2003 | Kiefer et al. | |
| 6,670,183 B2 | 12/2003 | Serrero | |
| 6,720,159 B1 | 4/2004 | Serrero | |
| 6,824,775 B2 | 11/2004 | Serrero | |
| 6,881,548 B2 | 4/2005 | Serrero | |
| 7,091,047 B2 | 8/2006 | Serrero | |
| 7,368,428 B2 | 5/2008 | Serrero | |
| 7,411,045 B2 | 8/2008 | Serrero et al. | |
| 2002/0094966 A1 | 7/2002 | Serrero | |
| 2003/0092661 A1 | 5/2003 | Serrero | |
| 2003/0215445 A1 | 11/2003 | Serrero | |
| 2004/0131618 A1 | 7/2004 | Serrero | |
| 2005/0106150 A1 | 5/2005 | Serrero | |
| 2005/0175616 A1 | 8/2005 | Kiener et al. | |
| 2007/0015225 A1 | 1/2007 | Serrero | |
| 2007/0065887 A1 | 3/2007 | Kinch et al. | |
| 2008/0114070 A1 | 5/2008 | Serrero | |
| 2008/0145369 A1 | 6/2008 | Serrero | |
| 2008/0311120 A1 | 12/2008 | Serrero et al. | |
| 2009/0010931 A1 | 1/2009 | Serrero | |
| 2009/0203047 A1 | 8/2009 | Serrero | |

FOREIGN PATENT DOCUMENTS

| | | |
|---|---|---|
| WO | WO-9115510 | 10/1991 |
| WO | WO-93/15195 | 8/1993 |
| WO | WO-98/52607 A1 | 3/1998 |
| WO | WO-02/31198 | 4/2002 |
| WO | WO-02102229 | 12/2002 |
| WO | WO-02102306 | 12/2002 |
| WO | WO-2004039244 | 5/2004 |
| WO | WO-2004045544 | 6/2004 |
| WO | WO-2004060280 | 7/2004 |
| WO | WO-2004078782 | 9/2004 |
| WO | WO-2005/000207 | 1/2005 |
| WO | WO-2005000240 | 1/2005 |
| WO | WO-2005011590 | 2/2005 |
| WO | WO-2006044566 | 4/2006 |

OTHER PUBLICATIONS

Ezzell (J. NIH Res, 1995, 7:46-49).*
Spitler (Cancer Biotherapy, 1995, 10:1-3).*
Boon (Adv Can Res, 1992, 58:177-210).*
Weiner L.M., Seminars Oncology, vol. 26, No. 4, Suppl 12, pp. 41-50, 1999.*
J. Barnwell, et al., "A Human 88-kD Membrane Glycoprotein (CD36) Functions in Vitro as a Receptor for a Cytoadherence Ligand on Plasmodium falciparum-infected Erythrocytes," J. Clin. Invest., Sep. 1989, vol. 84, pp. 765-772.
A. Bateman et al., "Granulins, a Novel Class of Peptide from Leukocytes," Biochemical and Biophysical Research Communications, vol. 173, No. 3, 1990, pp. 1161-1168.
V. Bhandari et al., "Isolation and sequence fo the granulin precursor cDNA from human bone marrow reveals tandem cysteine-rich granulin domains," Proc. Natl. Acad. Sci. USA, vol. 89, Mar. 1992, pp. 1717-1719.
R. Daniel, et al., "Cellular localization of Gene Expression for Progranulin," Journal of Histochemistry and Cytochemistry, Jul. 2000, vol. 48, No. 7, pp. 999-1009.
Hoque, et al., "The growth factor granulin interacts with cyclin T1 and modulates P-TEfb-dependent transcription," Mol Cell Biol., Mar. 2003, vol. 23, No. 5, pp. 1688-1702.
MB Jones et al., "The granulin-epithelin precursor/PC-cell-derived growth factor is a growth factor for epithelial ovarian cancer," Clin Cancer Res., Jan. 2003, vol. 9, No. 1, pp. 44-51.
WE Kim et al., "PC cell-derived growth factor stimulates proliferation and confers Trastuzumab resistance to Her-2-overexpressing breast cancer cells," Clin Cancer Res. Jul. 15, 2006, vol. 12, pp. 4192-4199.

(Continued)

Primary Examiner—Laura B Goddard
(74) Attorney, Agent, or Firm—Womble Carlyle Sandridge & Rice PLLC

(57) ABSTRACT

Methods and compositions for restoring growth inhibition sensitivity to a tumor cell resistant to growth inhibition by HER2 antagonists. The methods involve administering a PCDGF antagonist to the cell in an amount effective to stimulate or restore growth inhibition sensitivity to HER2 antagonists. The invention also provides treatment regimens, and therapeutic compositions comprising an HER2 antagonist and a PCDGF antagonist.

32 Claims, 14 Drawing Sheets

OTHER PUBLICATIONS

C. Landry, et al., Expression of Oligodendrocytic mRNAs in Glial Tumors: Changes Associated with Tumor Grade and Extent of Neoplastic Infiltration[1], Cancer Research, Sep. 15, 1997, vol. 57, pp. 4098-4104.

L. M. Liau, et al., "Identification of a Human Glioma-associated Growth Factor Gene, *granulin,* Using Differential Immuno-absorption[1]," Cancer Research, Mar. 1, 2000, vol. 60, pp. 1353-1360.

R. Lu et al., "Stimulation of PC cell-derived growth factor (epithelin/granulin precursor) expression by estradiol in human breast cancer cells," Biochem Biophys Res Commun., Mar. 5, 1999, vol. 256, No. 1, pp. 204-207.

R. Lu et al., "Resveratrol, a natural product derived from grape, exhibits antiestrogenic activity and inhibits the growth of human breast cancer cells," J Cell Physiol., Jun. 1999, vol. 179, No. 3, pp. 297-304.

G. Monami et al., "Proepithelin Regulates Prostate Cancer Cell Biology by Promoting Cell Growth, Migration, and Anchorage-Independent Growth", Am J. Pathol., Mar. 2009, vol. 174, No. 3, pp. 1037-1047.

CX. Pan et al., "PC cell-derived growth factor expression in prostatic intraepithelial neoplasia and prostatic adenocarcinoma," Clin Cancer Res., Feb. 15, 2004, vol. 10, No. 4, pp. 1333-1337.

G. Plowman et al., "The Epithelin Precursor Encodes Two Proteins with Opposing Activities on Epithelial Cell Growth," The Journal of Biological Chemistry, vol. 267, No. 18, 1992, pp. 13073-13078.

G. Serrero et al., "An In Vitro Model to Study Adipose Differentiation in Serum-Free Medium," Analytical Biochemistry, vol. 120, 1982, pp. 351-359.

G. Serrero, "Autocrine growth factor revisited: PC-cell-derived growth factor (progranulin), a critical player in breast cancer tumorigenesis," Biochem Biophys Res Commun., Aug. 29, 2003, vol. 3, pp. 409-413.

G. Serrero, "Endocrine and autocrine control of growth and differentiation of teratoma-derived cell lines," Prog. Clin. Bio. Res., 1986, vol. 226, pp. 191-204.

G. Serrero, et al., IHC Study of a novel molecular marker of infiltrating ductal carcinoma, The third Era of Hope meeting for the Department of Defense (DOD) Breast Cancer Research Program (BCRP) held Sep. 25-28, 2002.

W. Tangkeangsirisin et al., "PC cell-derived growth factor (PCDGF/GP88, progranulin) stimulates migration, invasiveness and VEGF expression in breast cancer cells," Carcinogenesis, Sep. 25, 2004, vol. 9, pp. 1587-1592.

W. Tangkeangsirisin et al., "PC cell-derived growth factor mediates tamoxifen resistance and promotes tumor growth of human breast cancer cell," Cancer Res. Mar. 1, 2004, vol. 64, No. 5, pp. 1737-1743.

H.E. Turner et al., "Expression analysis of cyclins in pituitary adenomas and the normal pituitary gland," Clinical Endocrinology, (2000), vol. 53, pp. 337-344.

H. Zhang et al., "Inhibition of tumorigenicity of the teratoma PC cell line by transfection with antisense cDNA for PC cell-derived growth factor (PCDGF, epithelin/granulin precursor)," Proc Natl Acad Sci USA Nov. 24, 1998, vol. 95, No. 24, pp. 14202-14207.

W. Wang et al., "PC cell-derived growth factor confers resistance to dexamethasone and promotes tumorigenesis in human multiple myeloma," Clin Cancer Res. Jan. 1, 2006, vol. 12, No. 1, pp. 49-56.

W. Wang et al., "PC-Cell Derived Growth Factor (PCDG, progranulin) Expression and Action in Human Multiple Myelomas," Proceedings of American Association for Cancer Research, Mar. 2001, vol. 42, p. 835.

W. Wang et al., "PC cell-derived growth factor (granulin precursor) expression and action in human multiple myeloma," Clin Cancer Res., Jun. 2003, vol. 9, No. 6, pp. 2221-2228.

X. Xia et al., "Identification of cell surface binding sites for PC cell-derived growth factor, PCDGF, (epithelin/granulin precursor) on epithelial cells and fibroblasts," Biochem Biophys Res Commun, Apr. 17, 1998, vol. 245, No. 2, pp. 539-543.

T. Zanocco-Marani, et al., "Biological Activities and Signaling Pathways of the Granulin/Epithelin Precursor," Cancer Research, Oct. 15, 1999, vol. 59, No. 20, pp. 5331-5340.

J. Zhou et al., "Purification of an Autocrine Growth Factor Homologous with Mouse Epithelin Precursor from a Highly Tumorigenic Cell Line," The Journal of Biological Chemistry, vol. 268, No. 15, 1993, pp. 10863-10869.

Z. He et al., "Progranulin Gene Expression Regulates Epithelial Cell Growth and Promotes Tumor Growth in Vivo[1]," Cancer Research 59, Jul. 1, 1999, pp. 3222-3229.

* cited by examiner

Nucleotide sequence of human granulin/epithelin precursor (human GP88).
Human Granulin Genbank M75161

```
cgcaggcaga ccatgtggac cttggtgagc tgggtggcct taacagcagg gctggtggct
ggaacgcggt gcccagatgg tcagttctgc cctgtggcct gctgcctgga ccccggagga
gccagctaca gctgctgccg tccccttctg gacaaatggc ccacaacact gagcaggcat
ctgggtggcc cctgccaggt tgatgcccac tgctctgccg gccactcctg catctttacc
gtctcaggga cttccagttg ctgccccttc ccagaggccg tggcatgcgg ggatggccat
cactgctgcc cacggggctt ccactgcagt gcagacggga gatcctgctt ccaaagatca
ggtaacaact ccgtgggtgc catccagtgc cctgatagtc agttcgaatg cccggacttc
tccacgtgct gtgtatggt cgatggctcc tgggggtgct gccccatgcc ccaggcttcc
tgctgtgaag acagggtgca ctgctgtccg cacggtgcct tctgcgacct ggttcacacc
cgctgcatca cacccacggg cacccacccc ctggcaaaga agctccctgc ccagaggact
aacagggcag tggccttgtc cagctcggtc atgtgtccgg acgcacggtc ccggtgccct
gatggttcta cctgctgtga gctgcccagt gggaagtatg gctgctgccc aatgcccaac
gccacctgct gctccgatca cctgcactgc tgcccccaag acactgtgtg tgacctgatc
cagagtaagt gcctctccaa ggagaacgct accacggacc tcctcactaa gctgcctgcg
cacacagtgg gcgatgtgaa atgtgacatg gaggtgagct gcccagatgg ctataccgc
tgccgtctac agtcgggggc ctggggctgc tgcccttta cccaggctgt gtgctgtgag
gaccacatac actgctgtcc cgcggggttt acgtgtgaca cgcagaaggg tacctgtgaa
caggggcccc accaggtgcc ctggatggag aaggccccag ctcacctcag cctgccagac
ccacaagcct tgaagagaga tgtccctgt gataatgtca gcagctgtcc ctcctccgat
acctgctgcc aactcacgtc tggggagtgg ggctgctgtc aatcccaga ggctgtctgc
tgctcggacc accagcactg ctgcccccag cgatacacgt gtgtagctga ggggcagtgt
cagcgaggaa gcgagatcgt ggctggactg gagaagatgc ctgcccgccg cggttcctta
tcccacccca gagacatcgg ctgtgaccag cacaccagct gcccggtggg cggaacctgc
tgcccgagcc agggtgggag ctgggcctgc tgccagttgc ccatgctgt gtgctgcgag
gatcgccagc actgctgccc ggctggctac acctgcaacg tgaaggctcg atcctgcgag
aaggaagtgg tctctgccca gcctgccacc ttcctggccc gtagccctca cgtgggtgtg
aaggacgtgg agtgtgggga aggacacttc tgccatgata accagacctg ctgccgagac
aaccgacagg gctgggcctg ctgtcctac gcccagggcg tctgttgtgc tgatcggcgc
cactgctgtc ctgctggctt ccgctgcgca cgcagggta ccaagtgttt gcgcagggag
gccccgcgct gggacgcccc tttgagggac ccagccttga cagctgct gtgagggaca
gtactgaaga ctctgcagcc ctcgggaccc cactcggagg gtgccctctg ctcaggcctc
gtactgaaga ctctgcagcc ctcgggaccc cactcggagg gtgccctctg ctcaggcctc
cctagcacct cccctaacc aaattctccc tggaccccat tctgagctcc ccatcaccat
gggaggtggg gcctcaatct aaggcccttc cctgtcagaa gggggttgag gcaaaagccc
attacaagct gccatcccct ccccgtttca gtggaccctg tggccaggtg cttttcccta
tccacagggg tgtttgtgtg ttgggtgtgc tttcaataaa gtttgtcact ttctt*
```

Nucleotide sequence of human PCDGF

FIG.1A

Amino-acid sequence of human granulin/epithelin precursor (human GP88).

MWTLVSWVALTAGLVAGTRCPDGQFCPVACCLDPGGASYSCCRP
LLDKWPTTLSRHLGGPCQVDAHCSAGHSCIFTVSGTSSCCPFPEAVACGDGHHCCPRG
FHCSADGRSCFQRSGNNSVGAIQCPDSQFECPDFSTCCVMVDGSWGCCPMPQASCCED
RVHCCPHGAFCDLVHTRCITPTGTHPLAKKLPAQRTNRAVALSSSVMCPDARSRCPDG
STCCELPSGKYGCCPMPNATCCSDHLHCCPQDTVCDLIQSKCLSKENATTDLLTYLPA
HTVGDVKCDMEVSCPDGYTCCRLQSGAWGCCPFTQAVCCEDHIHCCPAGFTCDTQKGT
CEQGPHQVPWM<u>EKAPAHLSLPDPQALKRD</u>VPCDNVSSCPSSDTCCQLTSGEWGCCPIP
EAVCCSDHQHCCPQRYTCVAEGQCQRGSEIVAGLEKMPARRGSLSHPRDIGCDQHTSC
PVGGTCCPSQGGSWACCQLPHAVCCEDRQHCCPAGYTCNVKARSCEKEVVSAQPATFL
ARSPHVGVKDVECGEGHFCHDNQTCCRDNRQGWACCPYAQGVCCADRRHCCPAGFRC<u>A
RRGTKCLRREAPRWDAPLRDPALRQLL</u>*

Deduced amino-acid sequence of human PCDGF

FIG. 1B

EKAPAHLSLPDPOALKRDV

FIG. 3A

RRGTKCLRREAPR

FIG. 3B

PCDGF AND erbB2 EXPRESSION
IN HUMAN BREAST CANCER BIOPSIES:

| ErbB2 | CASES # | PCDGF STAINING | | | | |
|---|---|---|---|---|---|---|
| 0 | n=9 | 0 | 1 | 2 | 3 | |
| 2 | n=6 | 1 | 1 | 4 | 3 | |
| 3 | n=7 | 2 | 3 | 1 | 0 | |
| | | 0 | 4 | 2 | 1 | |

FIG. 4

COMPOSITIONS AND METHODS FOR RESTORING SENSITIVITY TO TREATMENT WITH HER2 ANTAGONISTS

CROSS-REFERENCE TO RELATED APPLICATIONS

This application is a continuation of U.S. application Ser. No. 10/902,374 filed Jul. 30, 2004 now U.S. Pat. No. 7,674,460 which claims the benefit of U.S. Provisional Application Nos. 60/491,536 filed Aug. 1, 2003 and 60/547,791 filed Feb. 27, 2004, the contents of all of which are hereby incorporated by reference in their entireties. The following U.S. patents and U.S. Patent Publications are expressly incorporated by reference herein in their entireties: U.S. Pat. No. 6,720,159; U.S. Pat. No. 6,309,826, U.S. Patent Publication No. 2003/0099646, U.S. Patent Publication No. 2003/0215445 and U.S. Patent Publication No. 2002/0025543 (U.S. Pat. No. 6,881,548).

REFERENCES

Several publications are referenced herein. Full citations for these publications are provided below. The disclosures of these publications are hereby incorporated herein by reference in their entirety, unless otherwise noted.

BACKGROUND OF THE INVENTION

Approximately 25-30% of breast cancer patients overexpress the proto-oncoprotein and cell surface receptor c-erbB2 (human epidermal growth factor receptor 2 protein), also known as HER2/neu. Overexpression of the c-erbB2 oncogene has been linked to poor outcome and decreased survival for patients. The HER-2/neu protooncogene is overexpressed in 20-30% of metastatic breast cancers, and is associated with decreased survival and increased recurrence of breast cancer. HER-2/neu is also overexpressed in other cancer types including endometrial cancer, kidney cancer, gastric cancer, and prostate cancer. Presently, the most common form of treatment for these patients is the use of the humanized monoclonal antibody Trastuzumab, also known as Herceptin®.

Herceptin® is a recombinant DNA-derived humanized monoclonal antibody that selectively binds with high affinity (Kd=5 nM) to the extracellular domain of c-erbB2 in a cell-based assay. See Science 1985; 230:1132-9 and Cancer Res 1993; 53:4960-70. Herceptin® is an IgG1 kappa antibody that binds to HER2 and contains human framework regions with the complementarity-determining regions of a murine antibody (4D5). Id. However, only 25% of the patients treated with Herceptin® or any other antibody to c-erbB2/HER2 are responsive to this therapy. Several models have been postulated to explain resistance to treatment with c-erbB2/HER2 antibodies. What is needed are compositions and methods for restoring sensitivity to treatment with HER2/neu antagonists.

BRIEF SUMMARY OF THE INVENTION

The present invention is based, in part, on the discovery that an autocrine growth factor, PC-Cell Derived Growth Factor ("PCDGF"), confers resistance to the antineoplastic effects of c-erbB2/HER2 ("HER2") antagonists. Preferred embodiments of this invention are directed to therapeutic compositions and methods for restoring growth inhibition sensitivity to tumor cells resistant to the antineoplastic effects of HER2 antagonists by administering a PCDGF antagonist in an amount effective to stimulate or restore growth inhibition sensitivity to HER2 antagonists. In another embodiment, the invention provides a method to prevent recurrence of tumor growth using a PCDGF antagonist. Another embodiment of the invention provides therapeutic compositions and methods for inhibiting tumor cell growth comprising administering a PCDGF antagonist and an HER2 antagonist in an amount effective to inhibit tumor cell growth.

The invention also provides preferred compositions comprising an HER2 antagonist and a PCDGF antagonist. In another embodiment, the invention provides a pharmaceutical composition comprising an HER2 antagonist, a PCDGF antagonist, and a pharmaceutically-acceptable carrier (e.g., water, saline, Ringer's solution, dextrose solution, and human serum albumin).

Further embodiments of the invention provide methods of determining whether a patient is resistant to the antineoplastic effects of HER2 antagonists, comprising obtaining a biological sample containing cells from a patient; detecting PCDGF in the biological sample; and determining the amount of PCDGF in said sample wherein the amount of PCDGF is indicative of resistance to the antineoplastic effects of HER2 antagonists.

BRIEF DESCRIPTION OF THE DRAWINGS

FIGS. 1A and 1B shows the nucleotide sequence (SEQ ID NO:1) and deduced amino-acid sequence (SEQ ID NO:2), respectively, of the human PCDGF.

FIGS. 3A and 3B shows the 19 amino-acid sequence region defined as E19V (SEQ ID NO:3) and the 14 amino acid region defined as A14R (SEQ ID NO:4), respectively, of the human PCDGF.

FIG. 4 summarizes pathological studies in paraffin embedded human breast cancer biopsies. PCDGF and erbB2 staining were monitored by immunohistochemistry. Overexpression of PCDGF in cells which are also overexpressing erbB2 renders the cells resistant to HER2 antagonist. The numbers in the first column (down) and first row (across) indicate the intensity of staining for ErbB2 and PCDGF respectively on a scale of 0-3 with 3 being the highest level of intensity. Column 2 indicates the number of cases examined in each group. Rows 3-4 show the distribution of cases at each staining level for ErbB2 and PCDGF. For example, of the 6 cases showing a level 2 intensity for ErbB2 staining, 2 cases had a PCDGF staining intensity of 0, 3 cases had a PCDGF staining intensity of 1, 1 case had a PCDGF staining intensity of 2, and 0 had a PCDGF staining intensity of 3. It is known that 25% of patients with tumors that overexpress erbB2 will be responsive to HER2 antagonist therapy.

DETAILED DESCRIPTION OF THE INVENTION

Figure 2:
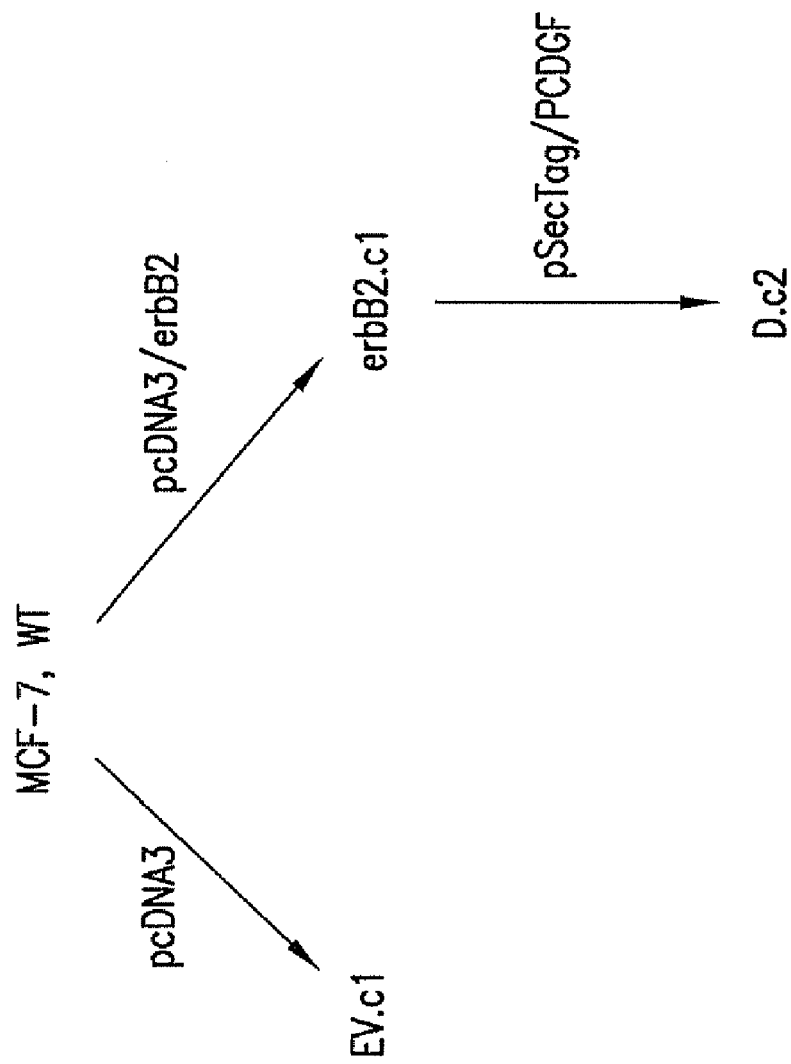
FIG. 2 shows a schematic diagram of producing a stable transfectant (D.c2) of MCF-7 cells that expressed both erbB2 and human PCDGF. As a control, cells transfected with pcDNA3 vector alone were also prepared (EV.c1).

PC-Cell Derived Growth Factor ("PCDGF") and HER2

PCDGF is an 88 kDa autocrine growth factor, having the nucleotide sequence and deduced amino-acid sequence of SEQ ID NOS:1 and 2, respectively, characterized in our laboratory and shown to be overexpressed in and induce tumorigenesis of a wide variety of human and animal tumor cells (e.g., neuroblastoma, glioblastoma, astrocytoma, sarcomas, and cancers of the prostate, blood, cerebrospinal fluid, liver, kidney, breast, head and neck, pharynx, thyroid, pancreas, stomach, colon, colorectal, uterus, cervix, bone, bone marrow, testes, brain, neural tissue, ovary, skin, and lung). See, e.g., U.S. Pat. No. 6,309,826, hereby incorporated by reference in its entirety.

PCDGF also confers resistance to the antineoplastic effects of HER2 antagonists (e.g., Herceptin®, HER2 kinase inhibitors; see infra) on tumor cells. As described in U.S. Pat. No. 6,309,826, overexpression of PCDGF leads to uncontrolled cell growth and increased tumorigenesis. The degree of PCDGF overexpression directly correlates with the degree of cellular tumorigenicity. Cells overexpressing PCDGF do not require external signals to maintain uncontrolled cell growth. Loss of regulated cell growth, such as a loss in responsiveness to insulin and/or estrogen, leads to increased malignancy and excessive unregulated cell growth. Development of methods and compositions that interfere with the tumorigenic activity of PCDGF is therefore of great interest for the treatment of cancer.

In a specific embodiment of the present invention, a method of stimulating or restoring growth inhibition sensitivity in a tumor patient who is resistant to growth inhibition by an HER2 antagonist, by administering a PCDGF antagonist to the patient in an amount effective to stimulate or restore growth inhibition sensitivity to an HER2 antagonist is provided. In another specific embodiment, the present invention provides a method of inhibiting tumor cell growth by administering a PCDGF antagonist and an HER2 antagonist to a patient in amounts effective to inhibit tumor cell growth. In yet another embodiment, the present invention provides a method of preventing tumor recurrence by administering a prophylactically effective amount of a PCDGF antagonist. The term "prophylactically effective amount" refers to an amount of a PCDGF antagonist or HER2 antagonist capable of preventing or delaying recurrence of tumor growth.

The term "HER2 antagonist" refers to any molecule (e.g., protein, antibody, peptide, small molecule, nucleic acid, antisense, or siRNA) that is capable of binding, interfering with, or inhibiting the activity of HER2 or any analogs or derivatives of HER2 that retain the neoplastic properties of HER2 (e.g., but not limited to Herceptin® and HER2 kinase inhibitors).

In one embodiment, an HER2 antagonist includes a molecule that can target or selectively bind to HER2 and, for example, deliver a toxin or other compound or molecule to kill a cell or inhibit cell growth. For example, an HER2 antibody can be coupled to a toxin or chemotherapeutic agent that is delivered to a tumor cell after the antibody binds to HER2. HER2 antagonists also include molecules (e.g., peptides, small molecules, antisense molecules, and siRNA) that modulate the biological activity of molecules that regulate the activity of HER2. An HER2 antagonist can be an antibody that recruits an immune response, e.g., through ADCC (antibody dependent cell cytotoxicity).

HER2 antagonist therapy is useful for treatment of patients with tumors that overexpress HER2, including but not limited to metastatic breast cancer, including patients whose tumors overexpress the HER2 protein and who have received one or more chemotherapy regimens for their metastatic disease. Herceptin®, in particular, is also approved for combination therapy with paclitaxel for treatment of patients with metastatic breast cancer whose tumors overexpress the HER2 protein and who have not received chemotherapy for their metastatic disease. However, only 25%-50% of the patients treated with Herceptin® or any other antibody to HER2 are responsive to such therapy. The present inventors have discovered that PCDGF confers resistance to the antineoplastic effects of HER2 antagonists. Immunohistochemistry studies in paraffin embedded human breast cancer biopsies showed that PCDGF was highly expressed in 40% of c-erbB2 positive (+3) invasive ductal carcinomas (see FIG. 4).

PCDGF Antagonist

The term "PCDGF antagonist" refers to any molecule (e.g., protein, antibody, peptide, small molecule, nucleic acid, antisense, or siRNA) that is capable of selectively binding, interfering with, or inhibiting the biological activity of PCDGF including, but not limited to, its ability to confer HER2-antagonist resistance to the cells exposed to PCDGF, or any analogs or derivatives of PCDGF that retain the properties of PCDGF. In one embodiment, a PCDGF antagonist includes PCDGF receptor antibodies or small molecule antagonist that can target or selectively bind to the PCDGF receptor and, for example, deliver a toxin or other compound or molecule to kill a cell or inhibit cell growth.

Antibodies

PCDGF antagonists, such as anti-PCDGF antibodies, interfere with the biological activity of PCDGF (e.g., tumorigenic activity) by binding PCDGF directly and preventing PCDGF from transmitting cell growth signals to a target cell (e.g., breast cancer cell). An anti-PCDGF antibody may bind the active site of PCDGF or its processed forms (e.g., the PCDGF receptor binding site) and prevent PCDGF from binding to its receptor. Alternatively, anti-PCDGF antibodies may bind to a site on PCDGF other than the active site, alter the conformation of the active site, and thus render PCDGF incapable of binding to its receptor. Anti-PCDGF antibodies include PCDGF neutralizing antibodies. "Neutralizing" antibodies have the ability to inhibit or block the normal biological activity of PCDGF, including PCDGF's ability to stimulate cell proliferation, increase cell survival, block apoptosis, or induce tumor growth in animals and in humans.

In one embodiment, an anti-PCDGF antibody or an antigen-binding fragment thereof immunospecifically binds the 19 amino-acid regions defined as E19V (SEQ ID NO:3) of human PCDGF. In another embodiment, an anti-PCDGF antibody or an antigen-biding fragment thereof binds the 14 amino-acid regions defined as A14R (SEQ ID NO:4) of human PCDGF. Anti-PCDGF antibodies suitable for restoring sensitivity to HER2 antagonist therapy and cytotoxic therapy, and in other preferred compositions and methods of the invention (e.g., inhibiting tumor cell growth, etc.) have been deposited in accordance with the Budapest Treaty with the American Type Culture Collection (ATCC), 10801 University Blvd., Manassas, Va. 20110-2209, and may be produced from hybridoma cell lines, including, but not limited to, 6B3 hybridoma cell line (ATCC Accession Number PTA-5262), 6B2 hybridoma cell line (ATCC Accession Number PTA-5261), 6C12 hybridoma cell line (ATCC Accession Number PTA-5597), 5B4 hybridoma cell line (ATCC Accession Number PTA-5260), 5G6 hybridoma cell line (ATCC Accession Number PTA-5595), 4D1 hybridoma cell line (ATCC Accession Number PTA-5593), 3F8 hybridoma cell line (ATCC Accession Number PTA-5591), 3F5 hybridoma cell line (ATCC Accession Number PTA-5259), 3F4 hybridoma cell line (ATCC Accession Number PTA-5590), 3G2 (ATCC Accession Number PTA-5592), 2A5 hybridoma cell line (ATCC Accession Number PTA-5589), and 4F10 (ATCC Accession Number PTA-8763) (anti-E19V monoclonal antibody). The hybridoma cell line designated 4F 10 has been deposited with the American Type Culture Collection (ATCC), 10801 University Blvd., Manassas, Va. 20110-2209 on Nov. 8, 2007, under Patent Deposit Designation PTA-8763. All restrictions imposed by the depositor on the availability to the public of the deposited material will be irrevocably removed upon granting of the patent.

PCDGF antagonists also include antibodies that immunospecifically bind a PCDGF receptor and block the binding of PCDGF to the receptor. Such anti-PCDGF receptor antibodies include antibodies produced from hybridoma cell lines including, but not limited to, 6G8 hybridoma cell line (ATCC Accession Number PTA-5263) and 5A8 hybridoma cell line (ATCC Accession Number PTA-5594).

The term antibody used herein refers to an antibody or an antigen-binding fragment thereof that immunospecifically binds to PCDGF, PCDGF receptor or HER2. In other words, an immunospecific antibody is specific for its antigen target (e.g., does not non-specifically bind to or associate with other antigens). Preferably such antibodies do not cross-react with other antigens. These specific antibodies include but are not limited to human and non-human polyclonal antibodies, human and non-human monoclonal antibodies (mAbs), chimeric antibodies, anti-idiotypic antibodies (anti-IdAb), neutralizing antibodies, non-neutralizing antibodies, and humanized antibodies and fragments thereof.

Polyclonal antibodies are heterogeneous populations of antibody molecules derived either from sera of animals immunized with an antigen or from chicken eggs and can be obtained by any suitable method known to one with ordinary skill in the art. The term "monoclonal antibody" refers to an antibody that is derived from a single clone, including any eukaryotic, prokaryotic, or phage clone, and not the method by which it is produced. Monoclonal antibodies ("mAbs") may be obtained by any suitable method, including the use of hybridoma, recombinant, and phage display technologies, or a combination thereof, which are within the knowledge of one skilled in the art.

Such antibodies may be of any immunological class including IgG, IgM, IgE, IgA, IgD and any subclass thereof. Antibody fragments which recognize specific epitopes include Fab and F(ab')2 fragments, which lack the Fc fragment of intact antibody, clear more rapidly from the circulation, and may have less non-specific tissue binding than an intact antibody. Such fragments are typically produced by proteolytic cleavage, using enzymes such as papain (to generate Fab fragments) and pepsin (to generate $F(ab')_2$ fragments). Antibodies or antigen-binding fragment thereof can also be produced by any method known in the art for the synthesis of antibodies, in particular, by chemical synthesis or preferably, by recombinant expression techniques.

Once an antibody molecule of the invention has been produced by any methods described above, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies of the present invention or fragments thereof may be fused to heterologous polypeptide sequences known in the art to facilitate purification, confer additional biological activities and so forth.

Nucleic Acid Interference

In another specific embodiment, PCDGF antagonists are nucleic acid molecules, including but not limited to antisense polynucleotides, RNA interference molecules, ribozymes, triple helix polynucleotides and the like, where the nucleotide sequence of such compounds are related to the nucleotide sequences of DNA and/or RNA of the PCDGF gene that are linked to the initiation of mRNA transcription.

In a specific embodiment, the nucleic acid molecule to be used as a PCDGF antagonist in nucleic acid interference comprises at least 10, 12, 14, 16, 18, 20, 22, 24, 26, 28, 30, 32, 36, 38 or 40 contiguous nucleotides of the nucleotide sequence of human PCDGF (SEQ ID NO:1). Such interfering nucleic acid molecules can be targeted against any suitable sequence. In one embodiment, the nucleic acid molecule is DNA. In another embodiment, the nucleic acid molecule is RNA, which may be single- or double-stranded.

Antisense technology has been the most commonly described approach in protocols to achieve gene-specific interference. For antisense strategies, stoichiometric amounts of single-stranded nucleic acid complementary to the messenger RNA for the gene of interest are introduced into the cell. See, e.g., U.S. Pat. No. 6,506,559, which is incorporated herein by reference in its entirety.

In one embodiment, the term "antisense oligonucleotides" corresponds to an RNA sequence as well as a DNA sequence coding therefore, which is sufficiently complementary to a particular mRNA molecule, for which the antisense RNA is specific, to cause molecular hybridization between the antisense RNA and the mRNA such that translation of the mRNA is inhibited. Such hybridization can occur under in vivo conditions.

The constitutive expression of PCDGF antisense RNA or DNA in tumor cells inhibits the expression of endogenous PCDGF expression and inhibits tumorigenicity of the antisense RNA or DNA transfected cells (see U.S. Pat. No. 6,309,826). The antisense molecule must have sufficient complementarity, about 18-30 nucleotides in length, to the PCDGF gene so that the antisense molecule can hybridize to the PCDGF gene or mRNA and inhibit PCDGF gene expression at the level of splicing, transcription, and/or translation.

The PCDGF antisense molecule may be hybridizable to any of several portions of the target nucleic acid molecule, including the coding sequence, 3' or 5' untranslated regions, or other intronic sequences, or to mRNA.

An antisense molecule may be delivered to a cell by transformation or transfection via a vector (e.g., retroviral vectors and plasmids), into which has been placed the DNA encoding the antisense RNA linked to appropriate regulatory sequences resulting in expression of the antisense RNA in the cell. Stable transfection of various antisense expression vectors containing PDGF cDNA fragments in the antisense orientation have been performed. Delivery of an antisense molecule can also be achieved by liposomes.

In another preferred embodiment, antisense oligonucleotides are used for in vivo therapy. Antisense oligonucleotides having a size of at least 10, 12, 14, 16, 18, 20, 22, 24, 26, 28, 30, 32, 34, 36, 38 or 40 bases, preferably about 15-30 bases, in length and with sequences hybridizable to any of several portions of the target PCDGF cDNA, including the coding sequence, 3' or 5' untranslated regions, or other intronic sequences, or to PCDGF mRNA, are preferred. The target sequences are preferably selected from the sequences that have the most potent antisense effect. Preferably, PCDGF antisense oligonucleotides are stable, have a high resistance to nucleases, possess suitable pharmacokinetics to allow them to traffic to disease tissue at non-toxic doses, and have the ability to cross through plasma membranes.

In certain embodiments, an RNA interference (RNAi) molecule is used to decrease or inhibit expression of the nucleic acid against which the RNAi is directed. RNAi refers to the use of double-stranded RNA (dsRNA) or small interfering RNA (siRNA) to suppress the expression of a gene comprising a related nucleotide sequence. RNAi is also called post-transcriptional gene silencing (or PTGS). Since the only RNA molecules normally found in the cytoplasm of a cell are molecules of single-stranded mRNA, the cell has enzymes that recognize and cut dsRNA into fragments containing at least 10, 12, 14, 16, 18, 20, 22, 24, 26, 28, 30, 32, 34, 36, 38 or 40 base pairs, preferably about 21-25 base pairs (approximately two turns of a double helix and which are referred to as small interfering RNA or siRNA). The antisense strand of the fragment separates enough from the sense strand so that it hybridizes with the complementary sense sequence on a molecule of endogenous cellular mRNA. This hybridization triggers cutting of the mRNA in the double-stranded region, thus destroying its ability to be translated into a polypeptide. Introducing dsRNA corresponding to a particular gene thus knocks out the cell's own expression of that gene in particular tissues and/or at a chosen time. Thus, RNAi regulates gene expression via an ubiquitous mechanism by degradation of target mRNA in a sequence-specific manner. See McManus et al., 2002, Nat Rev Genet. 3:737-747. In mammalian cells, interfering RNA (RNAi) can be triggered by 21- to 23-nucleotide duplexes of siRNA. See, e.g., Lee et al., 2002, Nat Biotechnol 20: 500-505; Paul et al., 2002, Nat Biotechnol. 20:505-508; Miyagishi et al., 2002, Nat Biotechnol. 20:497-500; Paddison et al., 2002, Genes Dev. 16: 948-958.

Double-stranded (ds) RNA can be used to interfere with gene expression in many organisms including, but not limited to mammals, in particular, human. For example, dsRNA can be used as inhibitory RNA or RNAi of the function of a nucleic acid molecule of interest (i.e, PCDGF gene or mRNA) to produce a phenotype that is the same as that of a null mutant of a nucleic acid molecule of the invention (Wianny & Zernicka-Goetz, 2000, Nature Cell Biology 2: 70-75).

Many methods have been developed to make siRNA, e.g., chemical synthesis or in vitro transcription. Once made, the siRNA can be introduced directly into a cell to mediate RNA interference (see e.g., Elbashir et al., 2001, Nature 411: 494-498; Song, E, et al. RNA interference targeting Fas protects mice from fulminant hepatitis. Nat. Med. 2003; 9: 347-351; and Lewis, D L, et al. Efficient delivery of siRNA for inhibition of gene expression in postnatal mice. Nat. Genet. 2002; 32: 107-108). Alternatively, the siRNA can be encapsulated into liposomes to facilitate delivery into a cell (see, e.g., Sorensen, D R, et al. Gene silencing by systemic delivery of synthetic siRNAs in adult mice. J Mol Biol. 2003; 327: 761-766).

A number of expression vectors have also been developed to continually express siRNAs in transiently and stably transfected mammalian cells (see, e.g., Brummelkamp et al., 2002, Science 296: 550-553; Sui et al., 2002, PNAS 99(6): 5515-5520; Paul et al., 2002, Nature Biotechnol. 20: 505-508). Some of these vectors have been engineered to express small hairpin RNAs (shRNAs), which are processed in vivo into siRNA-like molecules capable of carrying out gene-specific silencing. In certain embodiments, an shRNA contains plasmid under the control of a promoter, preferably a U6 promoter (see e.g., Paul, C P, et al. Effective expression of small interfering RNA in human cells. Nat. Biotechnol. 2002; 20: 505-508). Another type of siRNA expression vector encodes the sense and antisense siRNA strands under control of separate pol III promoters (see e.g., Miyagishi and Taira, 2002, Nature Biotechnol. 20: 497-500). The siRNA strands from this vector, like the shRNAs of the other vectors, have 3' thymidine termination signals. The shRNA gene can be delivered via a suitable vector system, e.g., adenovirus, adeno-associated virus (AAV), or retrovirus (see, e.g., Xia, H, et al. siRNA-mediated gene silencing in vitro and in vivo. Nat. Biotechnol. 2002; 20: 1006-1010; and Barton, G M, et al. Retroviral delivery of small interfering RNA into primary cells. Proc. Natl. Acad. Sci. USA 2002; 99: 14943-14945). Silencing efficacy by both types of expression vectors is comparable to that induced by transiently transfecting siRNA.

The RNA may comprise one or more strands of polymerized ribonucleotide. It may include modifications to either the phosphate-sugar backbone or the nucleoside. For example, the phosphodiester linkages of natural RNA may be modified to include at least one of a nitrogen or sulfur heteroatom.

Modifications in RNA structure may be tailored to allow specific genetic inhibition while avoiding a general panic response in some organisms which is generated by dsRNA. Likewise, bases may be modified to block the activity of adenosine deaminase. RNA may be produced enzymatically or by partial/total organic synthesis; any modified ribonucleotide can be introduced by in vitro enzymatic or organic synthesis.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition. The RNA molecule may be at least 10, 12, 15, 20, 21, 22, 23, 24, 25, 26, 27, 28, 29 or 30 nucleotides in length.

RNA containing a nucleotide sequence identical to a portion of the target gene are preferred for inhibition. RNA sequences with insertions, deletions, and single point mutations relative to the target sequence have also been found to be effective for inhibition. Thus, sequence identity may be optimized by sequence comparison and alignment algorithms known in the art (see, e.g., Gribskov and Deveeux, Sequence Analysis primer, Stockton Press, 1991, and references cited therein) and calculating the percent difference between the nucleotide sequences by, for example, the smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES, pH 6.4, 1 mM EDTA, 50° C. or 70° C. hybridization for 12-16 hours; followed by washing). The length of the identical nucleotide sequences may be any suitable length, preferably at least 10, 25, 50, 100, 200, 300 or 400 bases.

In one embodiment, siRNAs are generated from single stranded oligonucleotides having the following sequences, respectively: 5'-AGGTTGATGCCCACTGCTCTG-3' (SEQ ID NO:5). which targets the human PCDGF nucleotide region beginning at nucleotide position 203 (FIG. 1A); 5'-GAGCAGUGGGCAUCAACCUGG-3' (SEQ ID NO:6) which targets the human PCDGF sequence beginning at position 223 of PCDGF; 5'-AGATCAGGTAACAACTCCGTG-3' (SEQ ID NO:7), which targets the human PCDGF sequence beginning at nucleotide 342; and 5'-GGACACTTCTGCCATGATAAC-3' (SEQ ID NO:8), which targets the human PCDGF sequence beginning at nucleotide 1569.

One hundred percent sequence identity between the RNA and the target gene is not required to practice the present invention. Thus, the RNA interference has the advantage of being able to tolerate sequence variations that might be expected due to genetic mutation, strain polymorphism, or evolutionary divergence.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see also WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands. RNA may be directly introduced into the cell (i.e., intracellularly); or introduced extracellularly into a cavity, interstitial space, into the circulation of a subject, introduced orally, or may be introduced by bathing a cell or tissue in a solution containing the RNA. Physical methods of introducing nucleic acids, for example, injection directly into the cell or extracellular injection into the subject, may also be used. Vascular or extravascular circulation, the blood or lymph system, and the cerebrospinal fluid are sites where the RNA may be introduced.

Physical methods of introducing nucleic acids include injection of a solution containing the RNA, bombardment by particles covered by the RNA, soaking the cell or tissue in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, promote annealing of the duplex strands, stabilize the annealed strands, or other-wise increase inhibition of the target gene.

Small Molecules

PCDGF antagonizing agents may comprise small molecules (e.g., reagents, transcription factors, other factors or hormones) that inhibit PCDGF expression or its biological activity, or compete with PCDGF binding, signaling or biological activity. Compared to other PCDGF antagonists, such as antibodies, peptides, or antisense oligonucleotides, small molecules may have unique advantages as PCDGF antagonists. Small molecule PCDGF antagonists may be less immunogenic, more stable, easier to cross the cell membrane, easier for oral administration, and easier for synthesis and modification, thereby being cost effective. In a preferred embodiment, the invention provides small molecules that (1) inhibit PCDGF post-translational modification and its secretion, (2) block PCDGF activity by competing with PCDGF for binding to PCDGF cell surface receptors, (3) inhibit the PCDGF signal transduction pathway (e.g., biochemical interactions induced by PCDGF binding to its receptor on the cell surface), or (4) interfere or inhibit with the PCDGF receptor. Small molecules may be synthesized in order to bind to or associate with particular active sites on PCDGF, PCDGF cell surface receptors, or other molecules. Small molecules can also be derived from natural sources and modified to bind to and/or inhibit PCDGF, PCDGF cell surface receptors, or other molecules.

Pharmaceutical Compositions and Kits

The invention also provides pharmaceutical compositions containing one or more HER2 antagonists and one or more PCDGF antagonists. Patients receiving both HER2 and PCDGF antagonists will benefit from the antineoplastic effects of each antagonist in that the PCDGF antagonist can stimulate or restore the HER2 antagonist sensitivity of patients resistant to HER therapy. In a specific embodiment, the HER2 antagonist is Herceptin®. In another specific embodiment, the PCDGF antagonist is an antibody or an antigen-binding fragment thereof. In another specific embodiment, the PCDGF antagonist is a nucleic acid molecule, small molecule or polypeptides. The pharmaceutical compositions of the present invention have utility in inhibiting tumor cell growth as well as preventing tumor recurrence in a subject and may be administered to such a subject.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see e.g., Wu and Wu, 1987 J. Biol. Chem., 262: 4429 4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g. oral mucosa, rectal and intestinal mucosa, etc.) and may be administered together with other biologically active agents. Administration can be systemic or local. In a preferred embodiment, it may be desirable to introduce the pharmaceutical compositions of the invention into the affected tissues by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g. in conjunction with a wound dressing after surgery, by injection, by means of a catheter, by means of a suppository, or by means of an implant, said implant being of a porous, non porous, or gelatinous material, including membranes, such as sialastic membranes, or fibers. In one embodiment, administration can be by direct injection at the site (or former site) of diseased tissues.

In another embodiment, the pharmaceutical composition can be delivered in a vesicle, in particular a liposome (see, e.g., Langer, 1990 Science 249: 1527-1533; Treat et al., in Liposomes in the Therapy of Infectious Disease and Cancer, Lopez Berestein and Fidler (eds.), Liss, New York, pp. 353-365 (1989); Lopez-Berestein, ibid., pp. 317-327; see generally ibid.).

In yet another embodiment, the pharmaceutical composition can be delivered in a controlled release system. In one embodiment, a pump may be used (see Langer, supra; Sefton, 1987 CRC Crit. Ref. Biomed. Eng. 14: 201; Buchwald et al., 1980 Surgery 88:507; and Saudek et al., 1989 N. Engl. J. Med. 321: 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983 J. Macromol. Sci. Rev. Macromol. Chem. 23: 61; see also Levy et al., 1985 Science 228:190; During et al., 1989 Ann. Neurol. 25:351; Howard et al., 1989, J. Neurosurg. 71:105). In yet another embodiment, a controlled release system can be placed in proximity of the composition's target, i.e., the breast tissue, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249: 1527-1533).

The pharmaceutical compositions of the present invention further comprises a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2 ethylamino ethanol, histidine, procaine, etc.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems. Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a preferred embodiment, the kit contains a HER2 antagonist or its pharmaceutically acceptable salt, and a PCDGF antagonist or its pharmaceutically acceptable salt, together with a pharmaceutically acceptable carrier. In a specific embodiment, the HER2 antagonist is Herceptin®. In another specific embodiment, the PCDGF antagonist is an antibody, nucleic acid molecule, small molecule, or polypeptides. In a preferred embodiment, the pharmaceutical kit of the present invention contains one or more of the ingredients of the pharmaceutical compositions of the invention in a unit-dosage form. The pharmaceutical kit of the present invention may further comprise adjuvants, antivirals, antibiotics, analgesic, anti-inflammatory agents, or other pharmaceutically acceptable excipients.

Therapeutic Methods

Preferred embodiments of the invention are directed to methods of stimulating or restoring growth inhibition sensitivity to tumor cells resistant to the antineoplastic effects of HER2 antagonists by administering a PCDGF antagonist to a human patient in an amount effective to stimulate or restore the patient's growth inhibition sensitivity to HER2 antagonists. In another embodiment, the present invention provides methods of inhibiting tumor cell growth by administering a PCDGF antagonist and an HER2 antagonist to a patient in amounts effective to inhibit tumor cell growth. In yet another embodiment, the invention provides methods of preventing recurrence of tumor growth by administering a PCDGF antagonist and an HER2 antagonist to a patient in amounts effective to prevent or delay recurrence of tumor growth. PCDGF antagonists can prevent tumor formation and growth of any tumor or cancer type, including but not limited to, neuroblastoma, glioblastoma, astrocytoma, sarcomas, and cancers of the prostate, blood, liver, kidney, breast, head and neck, pharynx, thyroid, pancreas, stomach, colon, colorectal, uterus, cervix, bone, bone marrow, testes, brain, neural tissue, ovary, skin, and lung.

In yet another embodiment, a subject's cells (e.g., tumor cells) are removed from the body, transfected with a polynucleotide encoding a HER2 antagonist and a PCDGF antagonist, and injected at the site of the tumor. Expression of the polynucleotides encoding the HER2 antagonist and PCDGF antagonist localizes the HER2 and PCDGF antagonists at the tumor site. A subject's cells (e.g., tumor cells) can also be directly transfected in the body (e.g., in situ) with a construct containing a nucleic acid encoding a HER2 antagonist and/or a PCDGF antagonist. Expression of the nucleic acid results in production of the HER2 antagonist and/or PCDGF antagonist inside the transfected cell.

For in vivo applications, PCDGF antagonists, and HER2 antagonists can be provided to a subject by a variety of administration routes and dosage forms (see supra under "Pharmaceutical Compositions and Kits"). A subject, preferably a human subject, suffering from a neoplastic condition, including but not limited to breast cancer, or other disease condition associated with increased HER2 and/or PCDGF expression, is treated consecutively or simultaneously with an HER2 antagonist and a PCDGF antagonist. In one embodiment, the HER2 antagonist and PCDGF antagonist are co-administered. In a specific embodiment, the HER2 antagonist and PCDGF antagonist are concurrently administered. In another specific embodiment, the HER2 antagonist and PCDGF antagonist are sequentially administered, preferably the level of PCDGF ascertained and, if elevated, the PCDGF antagonist being administered first.

Treatment with a PCDGF antagonist can precede, follow, or be conducted concurrently with treatment with an HER2 antagonist. Treatment with a PCDGF antagonist may precede or follow treatment with an HER2 antagonist by intervals ranging from minutes to weeks. In another embodiment, a PCDGF antagonist and an HER2 antagonist are administered in a way to ensure that a prolonged period of time does not elapse between the time of administration of each agent. For example, each antagonist can be administered to a patient within seconds, minutes, or hours of the other antagonist.

In a preferred embodiment, treatment with a PCDGF antagonist decreases c-erbB2 phosphorylation by at least 5%, 10%, 15%, 20%, 25% or more, preferably by at least 50%. In a further preferred embodiment, treatment with a PCDGF antagonist increases cells' HER2-antagonist sensitivity by at least two-fold, more preferably by at least three-fold.

In another embodiment of the invention, an HER2 antagonist in combination with a PCDGF antagonist and/or chemotherapy (e.g., paclitaxel, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, aromatase inhibitors (e.g., Arimidex® or anastrozole, Femera®, letrozole), estrogen down-regulators (e.g., Faslodex®), estrogen receptor binding agents, taxol, gemcitabien, navelbine, farnesyl-protein transferase inhibitors, transplatinum, 5-fluorouracil, vincristin, vinblastin andmethotrexate, or any analog or derivative or variant of the foregoing, can be used to treat metastatic breast cancer or cancers of a variety of tissues (e.g., neuroblastoma, glioblastoma, astrocytoma, sarcomas, and cancers of the prostate, blood, liver, kidney, breast, head and neck, pharynx, thyroid, pancreas, stomach, colon, colorectal, uterus, cervix, bone, bone marrow, testes, brain, neural tissue, ovary, skin, and lung). Combination therapy can be administered independently of diagnostic evaluation.

In a preferred modality of the invention, a breast cancer patient (e.g., having metastatic breast cancer and overexpressing HER2) is given HER2 antagonist treatment with, for example, Herceptin. Although, the patient exhibits some degree of tumor growth inhibition, her progress declines, and she becomes resistant to HER2 antagonist therapy. A biopsy or serum sampling is conducted and reveals that the patient has elevated levels of PCDGF. In another embodiment, the patient's PCDGF levels are determined prior to beginning HER2 antagonist therapy. The patient is then treated with a PCDGF antagonist alone, or co-administration of PCDGF antagonist and HER2 antagonist, to stimulate or restore sensitivity to HER2 antagonist therapy. Following treatment with PCDGF antagonist, the patient is again responsive to HER2 antagonist therapy. The PCDGF level of the patient is periodically monitored, for example, weekly or monthly throughout the HER2 therapy and a PCDGF antagonist provided to again stimulate or restore HER2 sensitivity if needed. Alternatively, the patient can continue to receive co-administration of PCDGF antagonist and HER2 antagonist.

The ranges of effective doses provided below are not intended to limit the invention and merely represent illustrative dose ranges. However, the most preferred dosage will be tailored to the individual subject as is understood and determinable by one of ordinary skill in the art given the teachings herein. The total dose required for each treatment may be administered by multiple doses or in a single dose. In one embodiment, effective amounts of each of an HER2 antibody and a PCDGF antibody are from about 0.01 ng to about 500 μg/ml and preferably from about 10 ng to about 100 μg/ml. In another embodiment, effective amounts of antibody are typically from about 0.01 μg to about 100 mg/kg body weight and preferably from about 10 μg to about 50 mg/kg.

In yet another embodiment, an HER2 antagonist and a PCDGF antagonist may be administered separately, administered together, alone or in conjunction with other therapeutics. In another embodiment, the amount of each antagonist administered will typically be in the range of about 0.1 to about 10 mg/kg of body weight, so long as the HER2 and PCDGF antagonists are administered to the patient in therapeutically effective amounts (i.e., amounts that eliminate and/or reduce the patient's tumor burden or restore sensitivity to the antineoplastic effects of any HER2 antagonists) or prophylactically effective amounts (i.e., amounts that prevent or delay recurrence of tumor growth).

A preferred treatment regimen comprises co-administration of an effective amount of an HER2 antagonist and a PCDGF antagonist over a period of one or several weeks and including between about one week and six months. In another embodiment, an HER2 antagonist can be provided in an initial dose of 4 mg/kg followed by 2 mg/kg intravenous (i.v.) weekly; or dose of 8 mg/kg initial dose followed by 4 mg/kg i.v. weekly. Treatment with a PCDGF antagonist can be provided, for example, in an initial dose of 4 mg/kg followed by 2 mg/kg intravenous (i.v.) weekly; or a dose of 8 mg/kg initial dose followed by 4 mg/kg i.v. weekly. Additional examples of regimens for cancer treatment that can be used for treatment with an HER2 antagonist, a PCDGF antagonist, and/or chemotherapeutic agents are disclosed in the following articles: Hamid, O., J Am Pharm Assoc, 2004 January-February; 44(1):52-8; Kubo et al., Anticancer Res. 2003 November December; 23(6a):4443-9; Slamon et al., N Engl J Med. 2001; 344:783-792; Baselga et al., Cancer Res 1998; 58:2825-2831; and Jones, et al., Ann Oncol. 2003 December; 14(12):1697-704.

The protocols and compositions of the invention are preferably tested in vitro, and then in vivo, for the desired therapeutic or prophylactic activity, prior to use in humans.

For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed. Anti-PCDGF antibodies and anti-PCDGF receptor antibodies (collectively "PCDGF-antagonist antibodies") can be provided to cells both in vitro and in vivo. For in vitro applications, PCDGF-antagonist antibodies can be added to cell culture medium at concentrations typically ranging from 0.01 ng to about 100 mg/ml of cell culture media and preferably from about 10 ng to about 50 mg/ml. Antibody may be administered alone or in conjunction with other therapeutics directed to the same disease.

Cells can also be transfected with DNA or RNA encoding PCDGF-antagonist antibodies or antigen-binding fragments thereof or vectors containing such DNA or RNA sequences. Transfected cells can be induced to make PCDGF-antagonist antibodies or antibody fragments using any suitable technique (e.g., inducible promoter, and multiple plasmid copies).

In one embodiment, reduced tumor cell growth or increased survival of the contacted cells indicates that the therapeutic agent is effective to treat the condition in the patient. Alternatively, therapeutic agents and methods may be screened using established cell lines, such as MCF-7 cells (tamoxifen-resistant human breast cancer cells) and 04 cells (PCDGF-overexpressing, tamoxifen-resistant MCF-7 cells). Compounds for use in therapy can be tested in suitable animal model systems prior to testing in humans, including but not limited to in rats, mice, chicken, cows, monkeys, rabbits, hamsters, etc. The principle animal models widely used are well known in the art.

EXAMPLES

Figure 5:
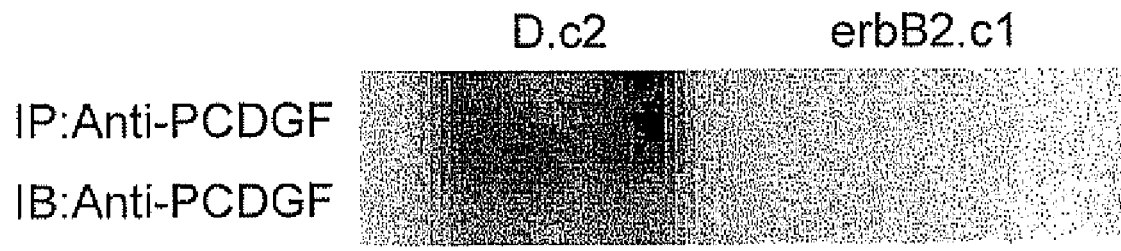
FIG. 5 shows the result of Western blot analysis detecting the PCDGF band in conditioned media from D.c2 cells, which overexpresses both erbB2 and PCDGF, using anti-PCDGF antibodies. The PCDGF band was detected by both immunoprecipitation (IP) and immunoblot (IM) of the conditioned media. No band was detected in the negative control (i.e., erB2.c1 clone which expresses erbB2 only).

PCDGF Confers Resistance to the Antineoplastic Effects of HER2 Antagonist Therapy Methods and Materials Preparation of Stable Transfectants To investigate the role of PCDGF in HER2 antagonist resistance of c-erbB2 overexpressing cells, MCF-7 breast cancer cells were stably transfected with pcDNA3/erbB2 expression vector (see FIG. 2) by the calcium phosphate method. A c-erbB2 overexpressing clone (erbB2.c1) was selected, and used for the subsequent stable transfection with pSecTag/PCDGF expression vector. Among the clones overexpressing both c-erbB2 and PCDGF, D.c2 clone was selected and further examined in comparison to single erbB2 overexpressing cells (see FIGS. 5, 6 and 7). Clones were established in the presence of Zeocin and/or G418.

Cell Proliferation Assay

Figure 11:
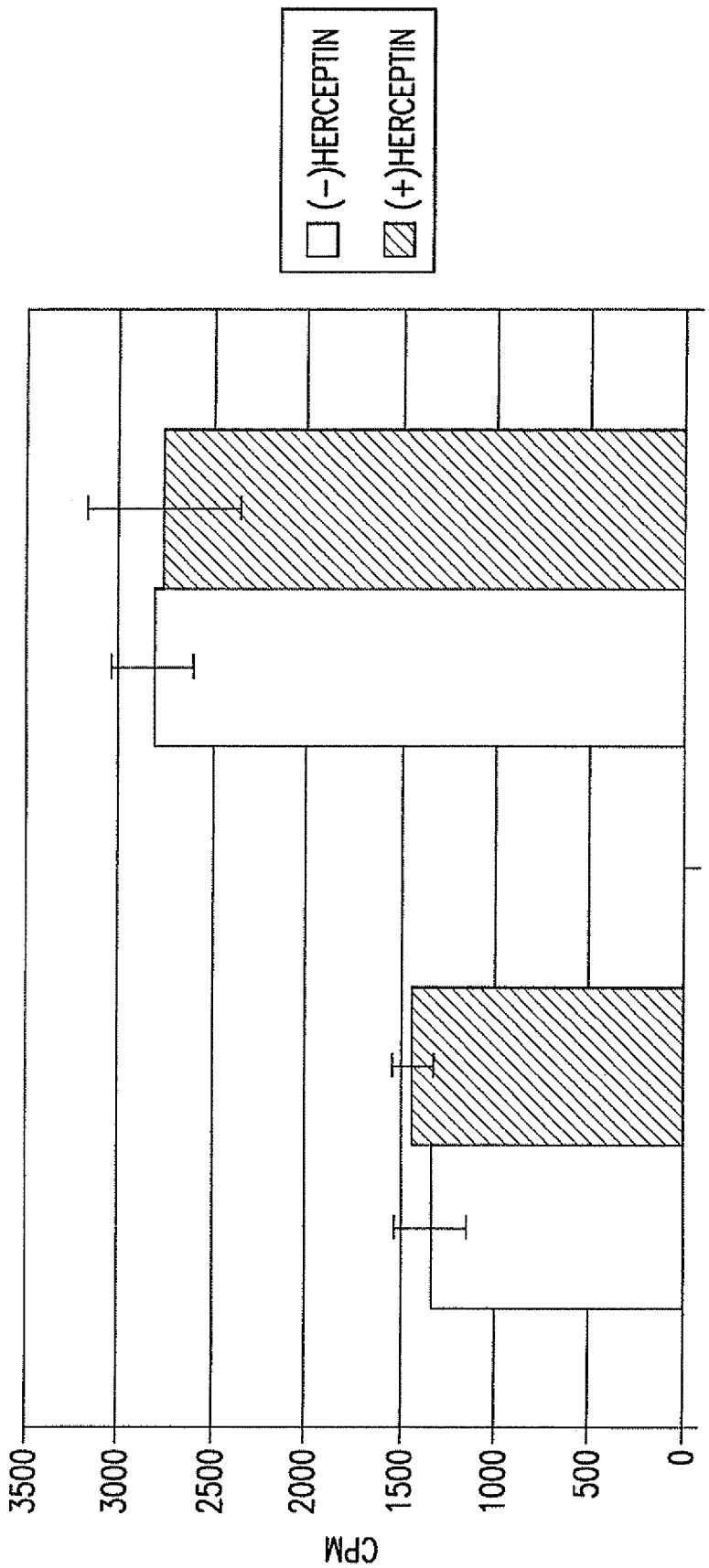
FIG. 11 shows that overexpression of PCDGF in erbB2 overexpressing cells confers resistance to the anti-proliferative activity of HER2/neu antagonists. HER2/neu antagonists no longer inhibit the proliferation of the breast cancer cells overexpressing both erbB2 and PCDGF as shown by thymidine incorporation as a measure of cell proliferation.
Figure 12:
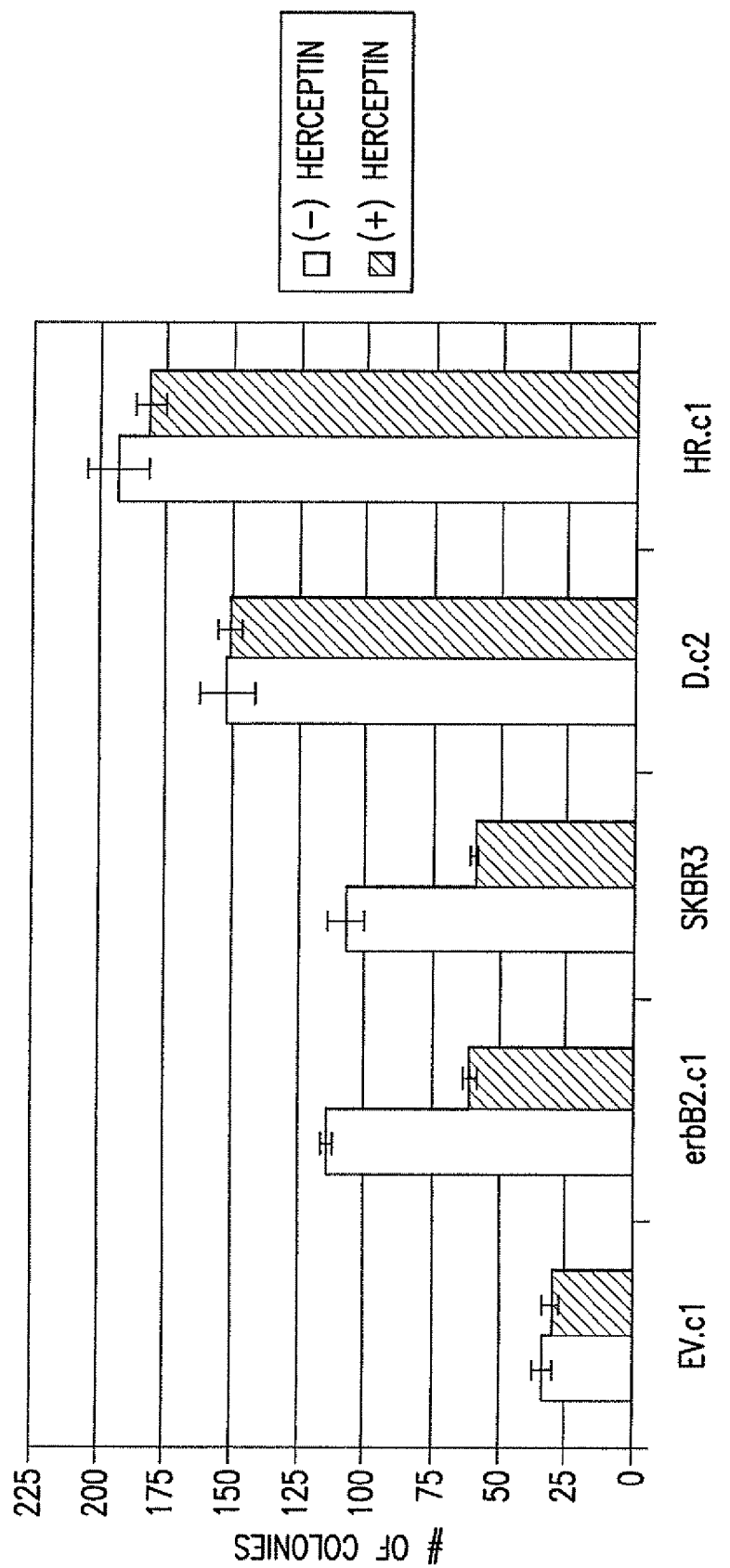
FIG. 12 shows the results of soft agar assays, which also demonstrate that PCDGF overexpression prevents HER2/neu antagonist inhibition of breast cancer cells in a soft agar (tumorigenesis) assay in erbB2 overexpressing cells. These results demonstrate that overexpression of PCDGF confers HER2/neu antagonist resistance in erbB2 overexpressing cells. EV.c1 is a MCF-7 cell transfected with a pcDNA3 alone. HR.c1 is a Herceptin® resistant cell.
Figure 13:
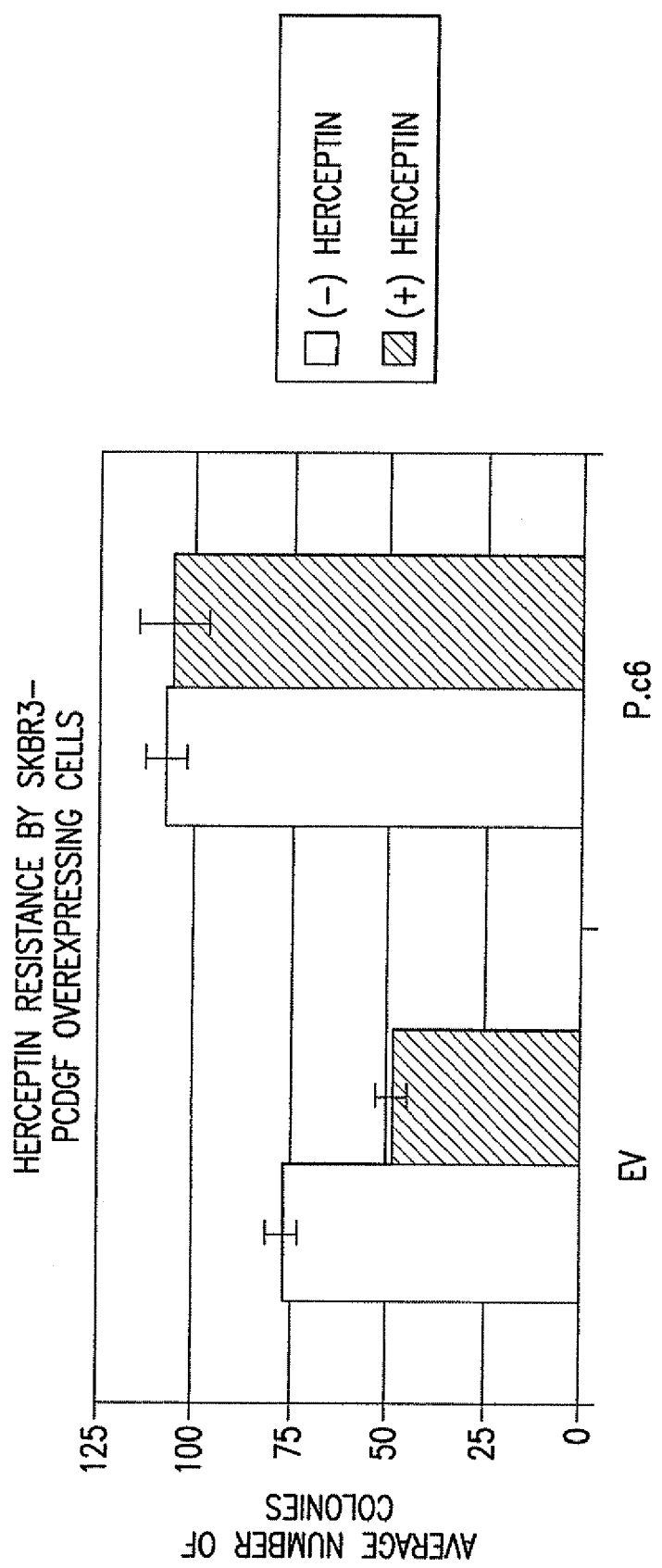
FIG. 13 shows HER2/neu antagonist resistance in SKBR3 cells overexpressing PCDGF. SKBR3 cells are breast cancer cells that naturally overexpress HER2. SKBR3 cells were transfected either with pcDNA3 empty vector (EV) or PCDGF expression vector in pcDNA3 (P.c6). In the latter case, PCDGF overexpression confers HER2/neu antagonist resistance on the cells.

The cells were plated in DMEF/F12 containing 5% FBS at $8 \times 10^4$ cells/well. After 24 hours of incubation, the cells were washed and fresh PFMEM was added along with various treatments. The cells were counted using a hemocytometer for each of the three days following the initial 24 hour incubation period (see FIGS. 11 and 12). As shown in FIGS. 11 and 12, overexpression of PCDGF confers HER2/neu antagonist resistance in cells overexpressing HER2/neu.

Thymidine Incorporation Assays

The cells were plated at $8\times10^4$ cells/well in DMEM/F12 containing 5% fetal bovine serum (FBS) in 24-well plates and incubated for 48 hours. The cells were then wasted, and fresh PEMEM (with or without 1% charcoal-tripped serum) was added along with the various treatments. Forty-eight hours later, 1 μCi of $^3$H-Thymidine was added to each well and the cells were incubated for 24 hours. The cell lysates were prepared and levels of $^3$H-thymidine were measured by liquid scintillation counter (see FIG. 11). As shown in FIG. 11, overexpression of PCDGF confers HER2/neu antagonist resistance in cells that overexpress HER2/neu.

Activation of erbB2

Two-hundred thousand ($2\times10^5$) cells were plated in DMEM/F12 containing 5% FBS and incubated for 48 hours. The cells were washed and added with fresh PFMEM (Phenol Red Free MEM) and further incubated for 24 hours. Various compounds were then added to the cells for up to 15 minutes. The cell lysates were prepared using RIPA buffer. The lysates were separated on a SDS-PAGE and transferred onto a PVDF membrane. After the transfer, the membrane was blocked and incubated with anti-phospho-erbB2 antibody followed by a labeled secondary antibody labeled. Positive bands were detected with enhanced chemiluminescence staining (ECL) (see FIGS. 6, 7 and 8). Heregulin was used as a positive control. These results show that PCDGF stimulates erbB2 phosphorylation in cells overexpressing erbB2 and indicate that PCDGF and erB2 share a common signal transduction pathway.

RT-PCR of PCDGF

The expression of PCDGF in erbB2 stable transfectants were measured by Reverse Transcription (RT)-PCR. Briefly, $2\times10^5$ cells were plated on 35 mm dishes in the appropriate medium. Forty-eight hours later, total RNA was extracted using Trizol® (Invitrogen) according to manufacturer's protocol. Superscript® II (Invitrogen) was used for the reverse transcription. The PCR was conducted by 25 cycles of [94° C., 1 min; 62° C., 45 sec; 72° C., 2 min] followed by a final elongation at 72° C. for 7 minutes. Samples were analyzed on a 1% agarose gel electrophoresis.

Western Blot Analysis

In one embodiment, one-hundred thousand ($1\times10^5$) cells/ ml were plated in the appropriate medium. Forty-eight hours later, cells were washed and fresh PFMEM was added. Twenty-four hours later, fresh PFMEM was added along with the indicated treatments. Cell lysates were collected using cell lysis buffer (50 mM Tris, pH 7.4; 4 mM EDTA; 25 mM KCl; 1 mM $Na_3VO_4$; 10 mM NaF; 1% Triton 100; 10 μg/ml leupeptin; 10 μg/ml pepstatin; and 2 μg/ml aprotinin). Forty μg of total protein lysates were loaded onto PAGE gels, and transferred onto PVDF membranes. For immunoprecipitations, 2 μg of anti-PCDGF was added to cell lysates and incubated overnight at 4° C. Forty μl of Protein A Sepharose was added and incubated at 4° C. for 4 hours. The Sepharose beads were washed with cold PBS, and protein sample buffer was added. Membranes were blocked with PBS-T (+5% milk) for 2 hours at room temperature. Membranes were incubated with the primary antibody overnight at 4° C. After washing with PBS-T three times (5 minutes each) membranes were incubated with the corresponding secondary antibody for 2 hours at room temperature. Membranes were washed three times (15 minutes each). Proteins were detected with enhanced chemiluminescence (EC).

Soft Agar Assay

Ten-thousand ($1\times10^4$) cells in 0.33% agarose were layered on top of −0.6% agarose in DMEM/F12 (+5% serum in general; 10% serum was used for SKBR3 cells). Colonies were grown for 21 days and then stained with 0.005% crystal violet. The colonies were counted using a microscope. As shown in FIG. 12, PCDGF overexpression confers resistance to HER2/neu antagonists in erbB2 overexpressing cells.

Results

Figure 6:
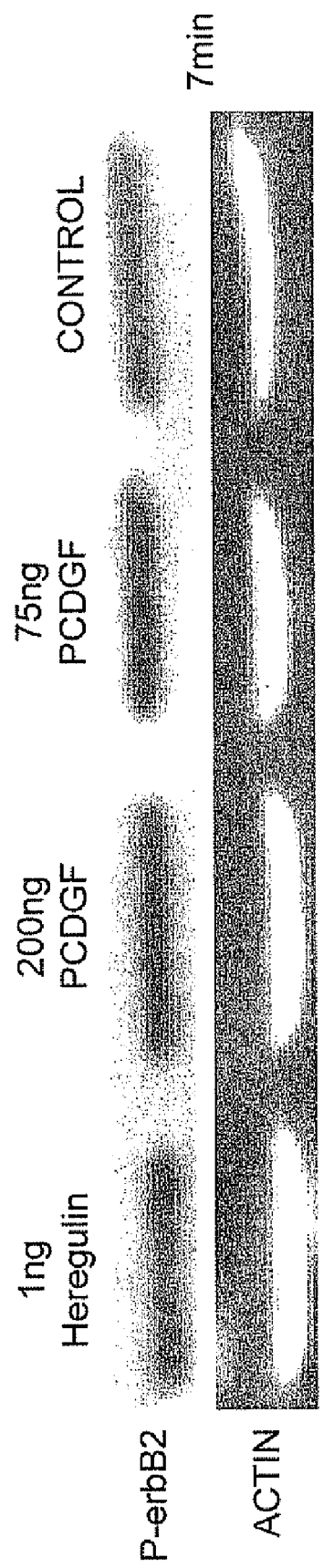
FIG. 6 shows the results of Western blot analysis, demonstrating the phosphorylation of erbB2 in erbB2.c1 cells which have been stimulated by different amounts (lane 2: 200 ng/ml; lane 3: 75 ng/ml; lane 4: 0 ng control) of PCDGF for 7 minutes. Phosphorylated erbB2 was detected with anti-phospho erbB2 antibody. As a positive control (lane 1), the cells were incubated with 10 ng of Heregulin.
Figure 7:
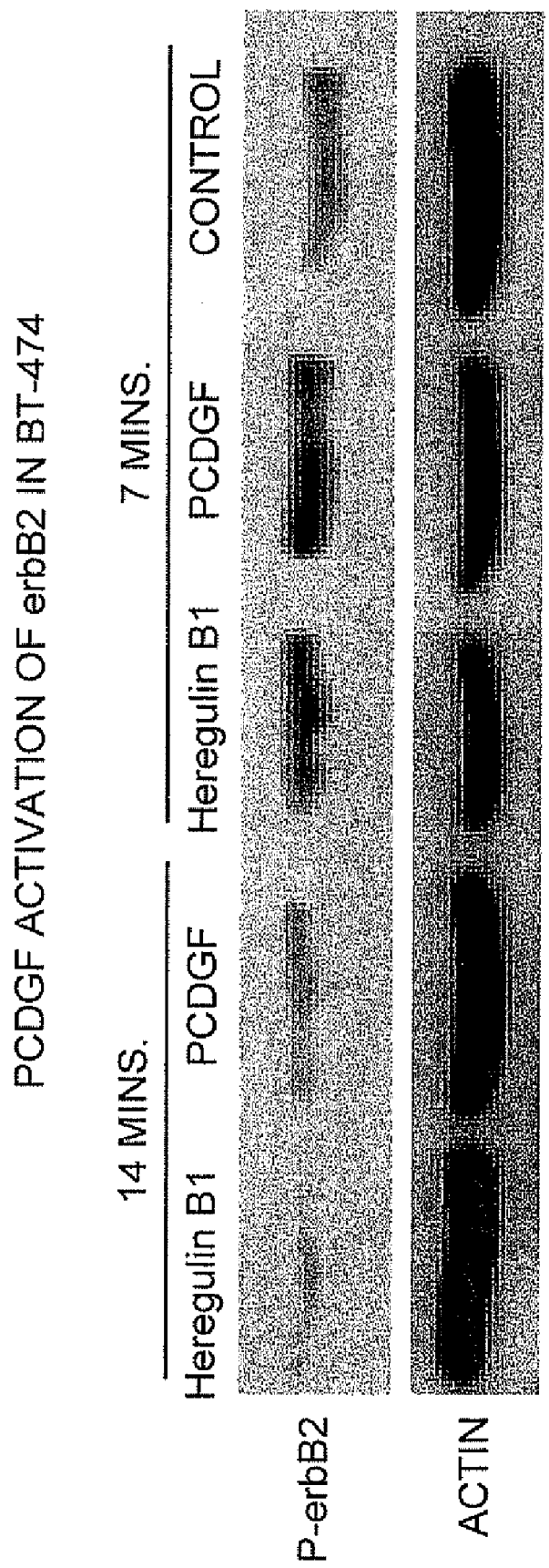
FIG. 7 shows the results of Western blot analysis, demonstrating that PCDGF stimulates erbB2 phosphorylation in other breast cancer cells, BT474 (shown here) and SKBR3 (see FIG. 13), that are known to overexpress erbB2. PCDGF was added at 200 ng/ml and Heregulin was added at 10 ng/ml.
Figure 8:
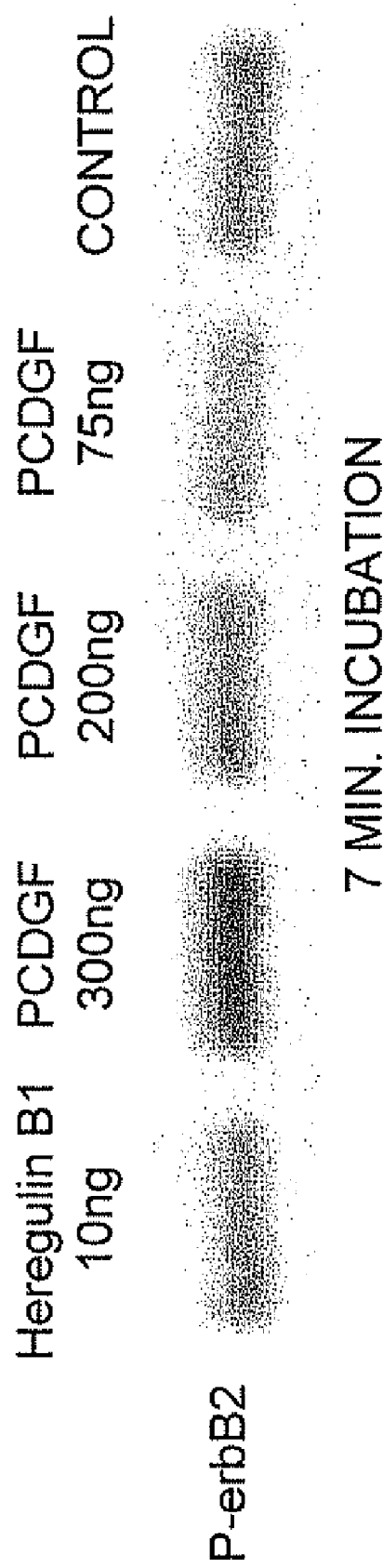
FIG. 8 shows the dose response of PCDGF stimulation of erbB2 in BT474 cells. PCDGF was added to the cells at 300 ng/ml, 200 ng/ml, 75 ng/ml and 0 ng/ml (control) and incubated for 7 minutes and phosphorylated erbB2 (P-erbB2) was detected by Western blot using anti-phospho erbB2 antibody. Ten nanograms of Heregulin β1 were used as a positive control.
Figure 9:
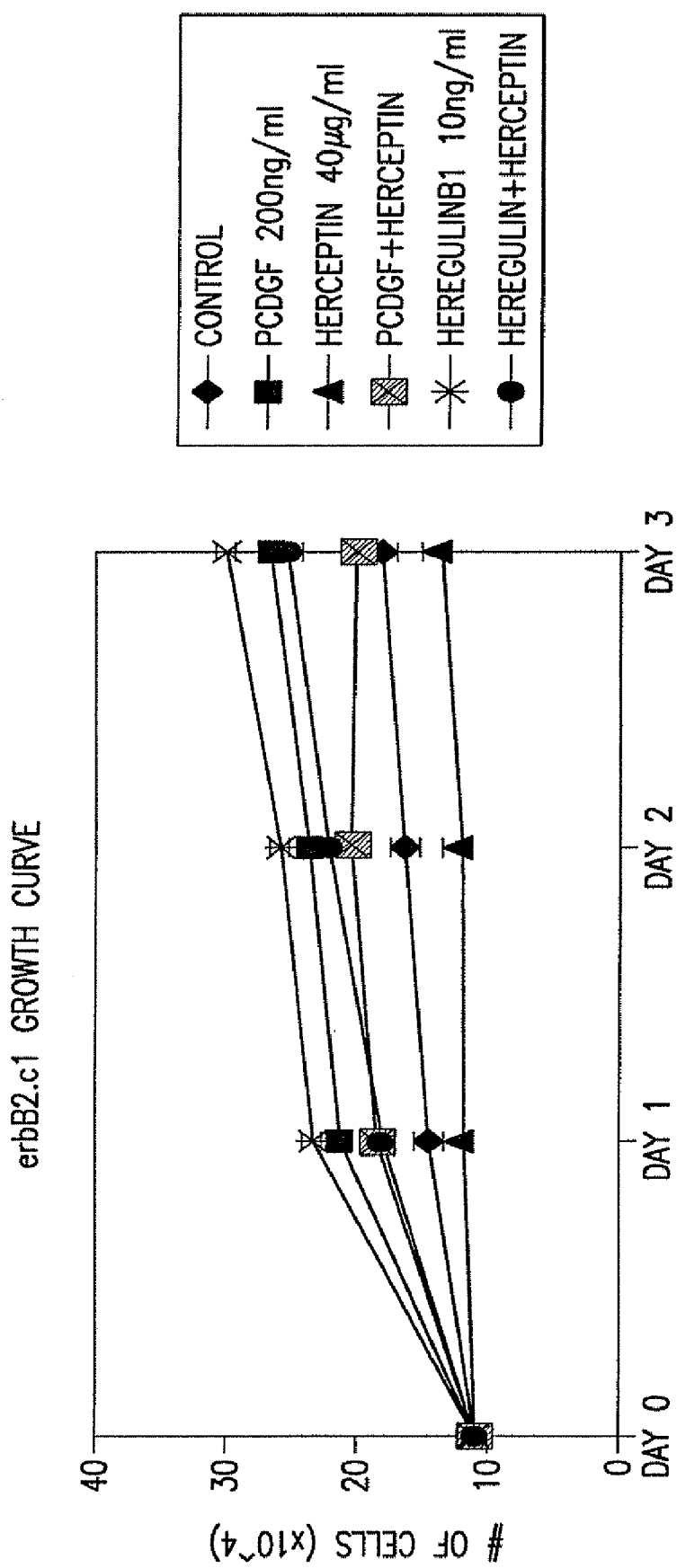
FIG. 9 shows the long term growth curves of erbB2.c1 cells in response to Herceptin®, PCDGF, and Heregulin, alone or in combination. Herceptin® inhibits proliferation of erbB2 overexpressing cells. Heregulin and PCDGF cause the cells to lose their sensitivity to HER2/neu antagonists.
Figure 10:
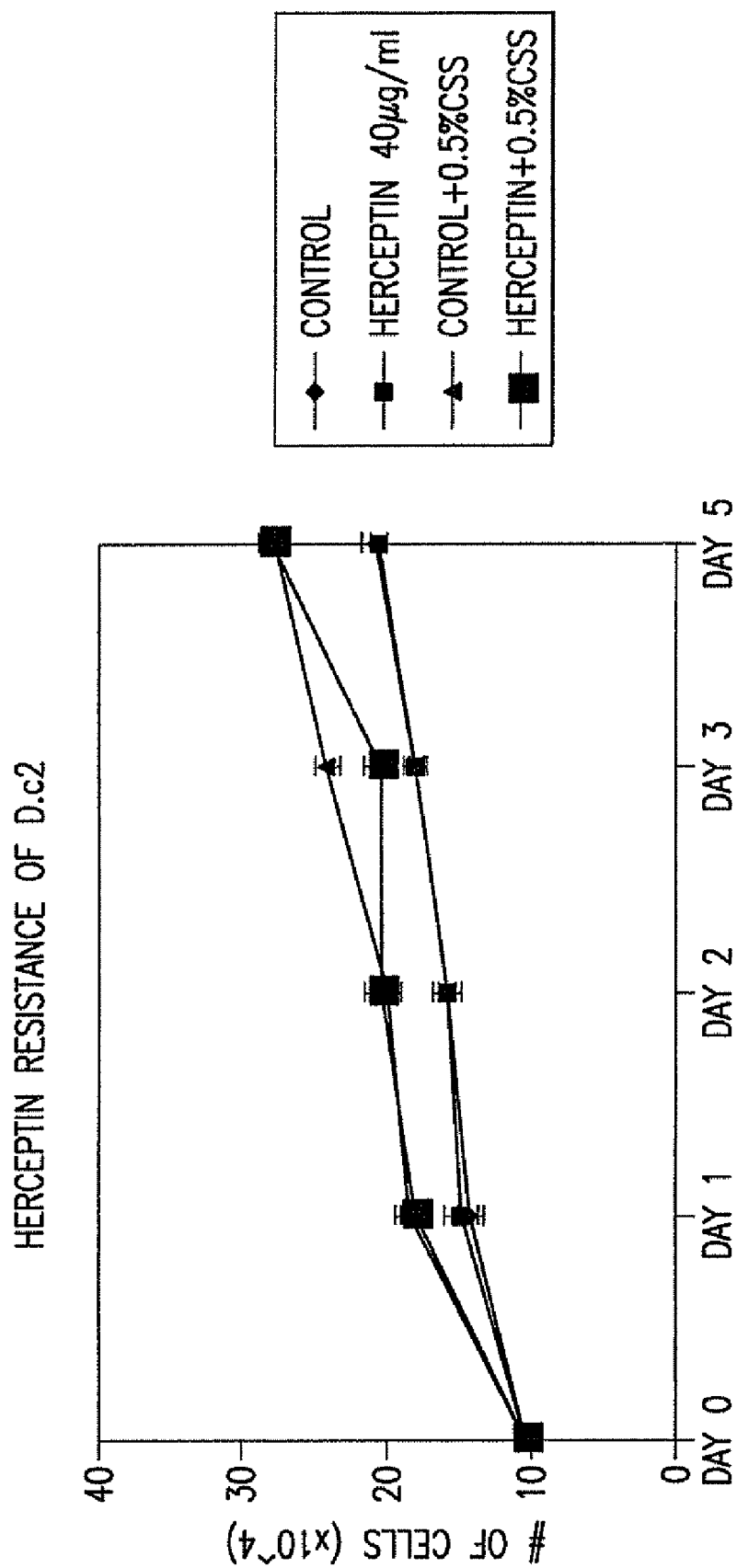
FIG. 10 shows the growth curves of PCDGF- and erbB2 overexpressing cells with or without Herceptin and 0.5% CSS. When PCDGF is overexpressed in the erbB2 overexpressing cells (e.g., D.c2 cells), HER2/neu antagonists no longer inhibit the proliferation of the breast cancer cells.

As shown in the appended Figures, dual-overexpressing clones (D.c2) (i.e., clones overexpressing both PCDGF and erbB2) were HER2-antagonist resistant with respect to their ability to proliferate in vitro (FIGS. 10 and 12), whereas the erbB2.c1 cells were sensitive to Herceptin® treatment (FIG. 9). These Herceptin®-sensitive erbB2.c1 cells also had a growth advantage when treated with PCDGF. Moreover PCDGF stimulates c-erbB2 phosphorylation in these cells (FIGS. 6 and 7). We have also shown that the dual expressing D.c2 cells were more resistant than the erbB2.c1 cells to the antiestrogen ICI 182,780 (data not shown). Our findings demonstrate that PCDGF confers Herceptin® resistance in c-erbB2 overexpressing tumors. Thus, blocking PCDGF action would be beneficial for patients undergoing HER2 antagonist treatment.

EQUIVALENTS

Those skilled in the art will recognize, or be able to ascertain many equivalents to the specific embodiments of the invention described herein using no more than routine experimentation. Such equivalents are intended to be encompassed by the following claims. Citation or discussion of a reference herein shall not be construed as an admission that such is prior art to the present invention.

What is claimed is:

1. An antibody produced by the hybridoma 4F10 (ATCC accession number PTA-8763) or an antigen-binding fragment thereof.

2. The antigen-binding fragment of claim 1, wherein said fragment is selected from Fab, F(ab)$_2$, Fab', F(ab')$_2$, Fd, Fd', Fv and scFv.

3. The antibody or fragment according to claim 1, wherein said antibody or fragment is chimerized.

4. The antibody or fragment according to claim 1, wherein said antibody or fragment is humanized.

5. A pharmaceutical composition comprising an antibody produced by the hybridoma 4F10 (ATCC accession number PTA-8763) or an antigen-binding fragment thereof.

6. The pharmaceutical composition of claim 5, where said fragment is selected from Fab, F(ab)$_2$, Fab', F(ab')$_2$, Fd, Fd', Fv and scFv.

7. The pharmaceutical composition of claim 5, wherein said antibody or fragment is chimerized.

8. The pharmaceutical composition of claim 5, wherein said antibody or fragment is humanized.

9. A kit comprising an antibody produced by the hybridoma 4F10 (ATCC accession number PTA-8763) or an antigen-binding fragment thereof.

10. A method of inhibiting tumor cell growth, comprising:
contacting the tumor cell with an antibody produced by the hybridoma 4F10 (ATCC accession number PTA-8763) or an antigen-binding fragment thereof.

11. The method of claim 10, wherein said tumor cell is selected from the group consisting of neuroblastoma, glioblastoma, astrocytoma, sarcomas, cancers of prostate, blood, cerebrospinal fluid, liver, kidney, breast, head and neck, pharynx, thyroid, pancreas, stomach, colon, colorectal, uterus, cervix, bone, bone marrow, testes, brain, neural tissue, ovary, skin, and lung.

12. The method of claim 10, wherein said fragment is selected from Fab, F(ab)$_2$, Fab', F(ab')$_2$, Fd, Fd', Fv and scFv.

13. The method of claim 10, wherein said antibody or fragment is chimerized.

14. The method of claim 10, wherein said antibody or fragment is humanized.

15. A method of inhibiting tumor growth in a patient, comprising:
administering to the patient a pharmaceutical composition comprising an antibody produced by the hybridoma 4F10 (ATCC accession number PTA-8763) or an antigen-binding fragment thereof.

16. The method of claim 15, wherein said patient is human.

17. The method of claim 15, wherein the tumor is selected from group of neuroblastoma, glioblastoma, astrocytoma, sarcomas, cancers of prostate, blood, cerebrospinal fluid, liver, kidney, breast, head and neck, pharynx, thyroid, pancreas, stomach, colon, colorectal, uterus, cervix, bone, bone marrow, testes, brain, neural tissue, ovary, skin, and lung.

18. The method of claim 15, wherein said fragment is selected from Fab, F(ab)$_2$, Fab', F(ab')$_2$, Fd, Fd', Fv and scFv.

19. The method of claim 15, wherein said antibody or fragment is chimerized.

20. The method of claim 15, wherein said antibody or fragment is humanized.

21. A method of treating tumor formation in a patient, comprising:
administering to the patient a pharmaceutical composition comprising an antibody produced by the hybridoma 4F10 (ATCC accession number PTA-8763) or an antigen-binding fragment thereof.

22. The method of claim 21, wherein said patient is human.

23. The method of claim 21, wherein the tumor is selected from group of neuroblastoma, glioblastoma, astrocytoma, sarcomas, cancers of prostate, blood, cerebrospinal fluid, liver, kidney, breast, head and neck, pharynx, thyroid, pancreas, stomach, colon, colorectal, uterus, cervix, bone, bone marrow, testes, brain, neural tissue, ovary, skin, and lung.

24. The method of claim 21, wherein said fragment is selected from Fab, F(ab)$_2$, Fab', F(ab')$_2$, Fd, Fd', Fv and scFv.

25. The method of claim 21, wherein said antibody or fragment is chimerized.

26. The method of claim 21, wherein said antibody or fragment is humanized.

27. A method of treating or preventing tumor recurrence in a patient, comprising:
   administering to the patient a pharmaceutical composition comprising an antibody produced by the hybridoma 4F10 (ATCC accession number PTA-8763) or an antigen-binding fragment thereof.

28. The method of claim 27, wherein said patient is human.

29. The method of claim 27, wherein the tumor is selected from group of neuroblastoma, glioblastoma, astrocytoma, sarcomas, cancers of prostate, blood, cerebrospinal fluid, liver, kidney, breast, head and neck, pharynx, thyroid, pancreas, stomach, colon, colorectal, uterus, cervix, bone, bone marrow, testes, brain, neural tissue, ovary skin, and lung.

30. The method of claim 27, wherein said fragment is selected from Fab, F(ab)$_2$, Fab', F(ab')$_2$, Fd, Fd', Fv and scFv.

31. The method of claim 27, wherein said antibody or fragment is chimerized.

32. The method of claim 27, wherein said antibody or fragment is humanized.

* * * * *

SEQUENCE LISTING

<160> NUMBER OF SEQ ID NOS: 8

<210> SEQ ID NO 1
<211> LENGTH: 2215
<212> TYPE: DNA
<213> ORGANISM: Homo sapiens

```
<400> SEQUENCE: 1
cgcaggcaga ccatgtggac cttggtgagc tgggtggcct aacagcagg gctggtggct      60
ggaacgcggt gcccagatgg tcagttctgc cctgtggcct gctgcctgga ccccggagga    120
gccagctaca gctgctgccg tccccttctg acaaatggc ccacaacact gagcaggcat     180
ctgggtggcc cctgccaggt tgatgccac tgctctgccg ccactcctg catctttacc      240
gtctcaggga cttccagttg ctgccccttc cagaggccg tggcatgcgg ggatggccat     300
cactgctgcc cacggggctt ccactgcagt gcagacgggc gatcctgctt ccaaagatca    360
ggtaacaact ccgtgggtgc catccagtgc cctgatagtc agttcgaatg cccggacttc    420
tccacgtgct gtgttatggt cgatggctcc tgggggtgct gccccatgcc ccaggcttcc    480
tgctgtgaag acagggtgca ctgctgtccg cacggtgcct tctgcgacct ggttcacacc    540
cgctgcatca cacccacggg cacccacccc ctggcaaaga agctccctgc ccagaggact    600
aacagggcag tggccttgtc cagctcggtc atgtgtccgg acgcacggtc ccggtgccct    660
gatggttcta cctgctgtga gctgccagt gggaagtatg gctgctgccc aatgcccaac     720
gccacctgct gctccgatca cctgcactgc tgccccaag acactgtgtg tgacctgatc     780
cagagtaagt gcctctccaa ggagaacgct accacggacc tcctcactaa gctgcctgcg    840
cacacagtgg gcgatgtgaa atgtgacatg gaggtgagct gcccagatgg ctataccctgc   900
tgccgtctac agtcggggc ctggggctgc tgccctttta cccaggctgt gtgctgtgag     960
gaccacatac actgctgtcc cgcggggttt acgtgtgaca cgcagaaggg tacctgtgaa   1020
caggggcccc accaggtgcc ctggatggag aaggccccag ctcacctcag cctgccagac   1080
ccacaagcct tgaagagaga tgtccctgt gataatgtca gcagctgtcc ctcctccgat   1140
acctgctgcc aactcacgtc tggggagtgg ggctgctgtc caatcccaga ggctgtctgc   1200
tgctcggacc accagcactg ctgcccccag cgatacacgt gtgtagctga ggggcagtgt   1260
cagcgaggaa gcgagatcgt ggctggactg gagaagatgc ctgcccgccg cggttcctta   1320
tcccacccca gagacatcgg ctgtgaccag cacaccagct gcccggtggg cggaacctgc   1380
tgcccgagcc agggtgggag ctgggcctgc tgccagttgc cccatgctgt gtgctgcgag   1440
gatcgccagc actgctgccc ggctggctac acctgcaacg tgaaggctcg atcctgcgag   1500
aaggaagtgg tctctgccca gcctgccacc ttcctggccc gtagccctca cgtgggtgtg   1560
aaggacgtgg agtgtgggga aggacacttc tgccatgata accagacctg ctgccgagac    1620
aaccgacagg gctgggcctg ctgtcccta cgccagggcg tctgttgtgc tgatcggcgc    1680
cactgctgtc ctgctggctt ccgctgcgca cgcagggta ccaagtgttt gcgcagggag   1740
gccccgcgct gggacgcccc tttgagggac ccagccttga cagctgct gtgagggaca    1800
gtactgaaga ctctgcagcc ctcgggaccc cactcggagg gtgccctctg ctcaggcctc   1860
gtactgaaga ctctgcagcc ctcgggaccc cactcggagg gtgccctctg ctcaggcctc   1920
gtactgaaga ctctgcagcc ctcgggaccc cactcggagg gtgccctctg ctcaggcctc   1980
cctagcacct cccctaacc aaattctccc tggacccat tctgagctcc ccatcaccat    2040
ggaggtggg gcctcaatct aaggcccttc cctgtcagaa ggggggttgag gcaaaagccc   2100
attacaagct gccatcccct cccgtttca gtggaccctg tggccaggtg ctttttcccta   2160
tccacagggg tgtttgtgtg ttgggtgtgc tttcaataaa gtttgtcact ttctt         2215
```

<210> SEQ ID NO 2
<211> LENGTH: 593
<212> TYPE: PRT
<213> ORGANISM: Homo sapiens

<400> SEQUENCE: 2

```
Met Trp Thr Leu Val Ser Trp Val Ala Leu Thr Ala Gly Leu Val Ala
  1               5                  10                  15

Gly Thr Arg Cys Pro Asp Gly Gln Phe Cys Pro Val Ala Cys Cys Leu
             20                  25                  30

Asp Pro Gly Gly Ala Ser Tyr Ser Cys Cys Arg Pro Leu Leu Asp Lys
                 35                  40                  45

Trp Pro Thr Thr Leu Ser Arg His Leu Gly Pro Cys Gln Val Asp
 50                  55                  60

Ala His Cys Ser Ala Gly His Ser Cys Ile Phe Thr Val Ser Gly Thr
 65                  70                  75                  80

Ser Ser Cys Cys Pro Phe Pro Glu Ala Val Ala Cys Gly Asp Gly His
                 85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
            115                 120                 125

Ser Gln Phe Glu Cys Pro Asp Phe Ser Thr Cys Cys Val Met Val Asp
        130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
                180                 185                 190

Ala Gln Arg Thr Asn Arg Ala Val Ala Leu Ser Ser Val Met Cys
            195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Tyr Leu Pro Ala His Thr Val Gly Asp Val Lys Cys Asp Met Glu Val
            275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
    370                 375                 380
```

```
Glu Trp Gly Cys Cys Pro Ile Pro Glu Ala Val Cys Cys Ser Asp His
385                 390                 395                 400

Gln His Cys Cys Pro Gln Arg Tyr Thr Cys Val Ala Glu Gly Gln Cys
            405                 410                 415

Gln Arg Gly Ser Glu Ile Val Ala Gly Leu Glu Lys Met Pro Ala Arg
        420                 425                 430

Arg Gly Ser Leu Ser His Pro Arg Asp Ile Gly Cys Asp Gln His Thr
        435                 440                 445

Ser Cys Pro Val Gly Gly Thr Cys Cys Pro Ser Gln Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
        515                 520                 525

Asp Asn Gln Thr Cys Cys Arg Asp Asn Arg Gln Gly Trp Ala Cys Cys
530                 535                 540

Pro Tyr Ala Gln Gly Val Cys Cys Ala Asp Arg Arg His Cys Cys Pro
545                 550                 555                 560

Ala Gly Phe Arg Cys Ala Arg Arg Gly Thr Lys Cys Leu Arg Arg Glu
            565                 570                 575

Ala Pro Arg Trp Asp Ala Pro Leu Arg Asp Pro Ala Leu Arg Gln Leu
            580                 585                 590

Leu

<210> SEQ ID NO 3
<211> LENGTH: 19
<212> TYPE: PRT
<213> ORGANISM: Homo sapiens

<400> SEQUENCE: 3

Glu Lys Ala Pro Ala His Leu Ser Leu Pro Asp Pro Gln Ala Leu Lys
 1               5                  10                  15

Arg Asp Val

<210> SEQ ID NO 4
<211> LENGTH: 13
<212> TYPE: PRT
<213> ORGANISM: Homo sapiens

<400> SEQUENCE: 4

Arg Arg Gly Thr Lys Cys Leu Arg Arg Glu Ala Pro Arg
 1               5                  10

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aggttgatgc ccactgctct g                                              21
```

-continued

```
<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gagcaguggg caucaaccug g                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agatcaggta acaactccgt g                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggacacttct gccatgataa c                                              21
```